(12) United States Patent  (10) Patent No.: US 8,815,532 B2
Kovalenko  (45) Date of Patent: Aug. 26, 2014

(54) COLOR-PRODUCING DIAGNOSTIC SYSTEMS, REAGENTS AND METHODS

(75) Inventor: Victor Kovalenko, Saco, ME (US)

(73) Assignee: Diagnostic Innovations, LLC, Saco, ME (US)

( * ) Notice: Subject to any disclaimer, the term of this patent is extended or adjusted under 35 U.S.C. 154(b) by 0 days.

(21) Appl. No.: 13/478,820

(22) Filed: May 23, 2012

(65) Prior Publication Data

US 2013/0023444 A1  Jan. 24, 2013

Related U.S. Application Data

(60) Provisional application No. 61/494,232, filed on Jun. 7, 2011.

(51) Int. Cl.
*C12Q 1/28* (2006.01)
(52) U.S. Cl.
USPC .......................................................... 435/28
(58) Field of Classification Search
None
See application file for complete search history.

(56) References Cited

U.S. PATENT DOCUMENTS

| 5,432,285 | A | 7/1995 | Theodoropulos et al. | |
| 5,492,821 | A * | 2/1996 | Callstrom et al. | 435/188 |
| 6,342,078 | B1 | 1/2002 | De La Mettrie et al. | |
| 6,680,204 | B1 | 1/2004 | Turner et al. | |
| 2007/0178542 | A1* | 8/2007 | Kovalenko | 435/7.32 |
| 2007/0254285 | A1 | 11/2007 | Zhelev et al. | |
| 2008/0145949 | A1 | 6/2008 | Song et al. | |

FOREIGN PATENT DOCUMENTS

EP  0308236 A2  3/1989

OTHER PUBLICATIONS

International Search Report for PCT/US2012/039147 dated Nov. 29, 2012.

* cited by examiner

*Primary Examiner* — Samuel Woolwine
*Assistant Examiner* — Kaijiang Zhang
(74) *Attorney, Agent, or Firm* — Foley Hoag LLP

(57) ABSTRACT

Provided herein are novel reagents and their use in color-producing detection systems for performing diagnostic tests and analytical assays.

25 Claims, 8 Drawing Sheets

Figure 2. Analysis of hydrogen donor conjugates spotted on glass fiber membrane

Spots with soluble conjugates  Spots with particle conjugates  Spots with soluble conjugates
Coupler/peroxide substrate                                       TMB membrane substrate

FIGURE 3
A. Fusion 5 glass fiber membrane (Assay time 2 min)
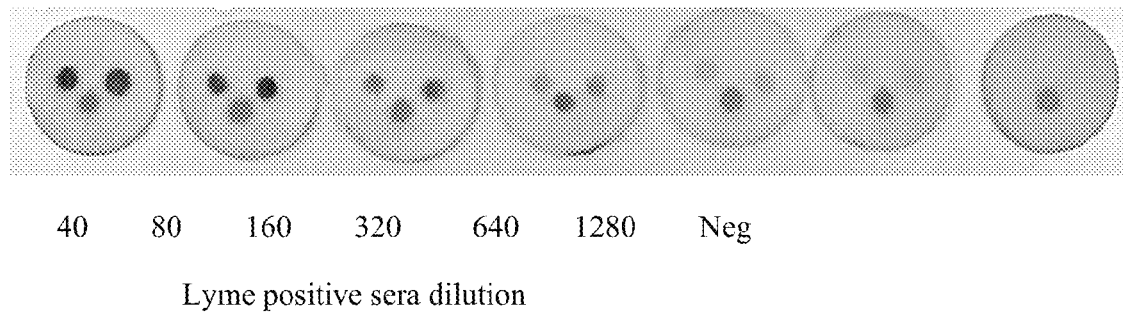
40    80    160    320    640    1280    Neg
Lyme positive sera dilution
B. Porous polyethylene matrix (Assay time 4-5 min)
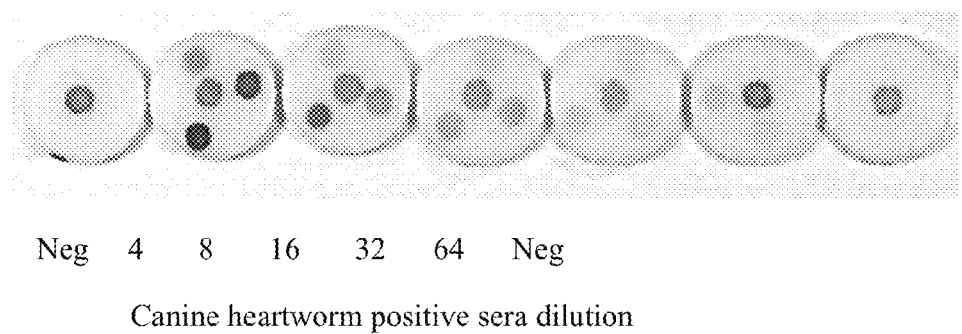
Neg    4    8    16    32    64    Neg
Canine heartworm positive sera dilution Neg   D1   D2   D3   D1+D2   D1+D3   D2+D3   D1+D2+D3

Neg- Negative sample, internal control spot-Violet
D1 positive test spot-Blue
D2 positive test spot-Red
D3 positive test spot-Rose
D1+D2 positive test spots-Red and Blue
D1+D3 positive test spots-Red and Rose
D2+D3 positive test spots-Blue and Rose
D1+D2+D3 positive test spots-Red, Blue and Rose

FIGURE 5
A.
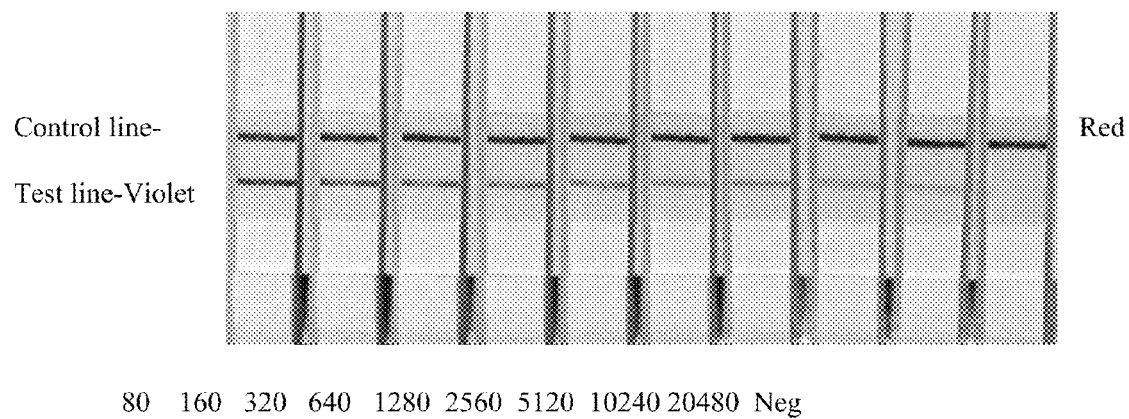
80  160  320  640  1280  2560  5120  10240  20480  Neg
B.
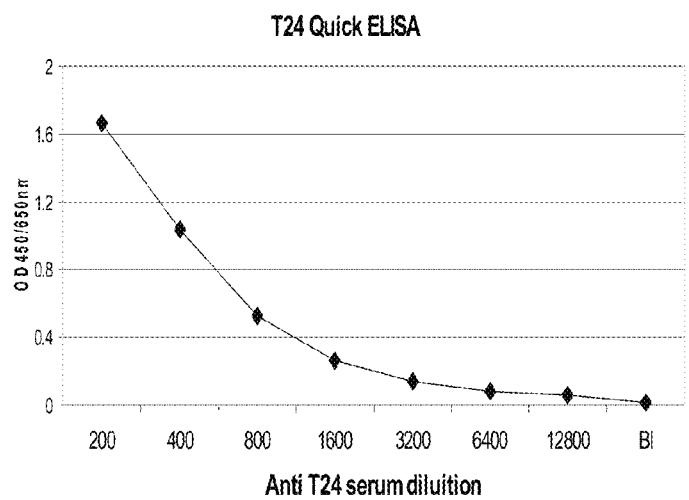

FIGURE 6  Lateral Flow test for detection of antibodies against Lyme C6 peptide on Porex porous polyethylene strips N1-Negative
N2-Low Positive, undetectable in ELISA
N3-Low positive
N4- Medium Positive in ELISA
N5 and N6 –High Positive Flow-through test on nitrocellulose membrane (Assay time 5-8 min)

Neg     1:80     1:5,120     1:81,920

Lyme positive sera dilution

Middle dashed line-internal positive control (Red)
Left solid line- C6 Test (Violet)
Right solid line – C10 test (Blue)

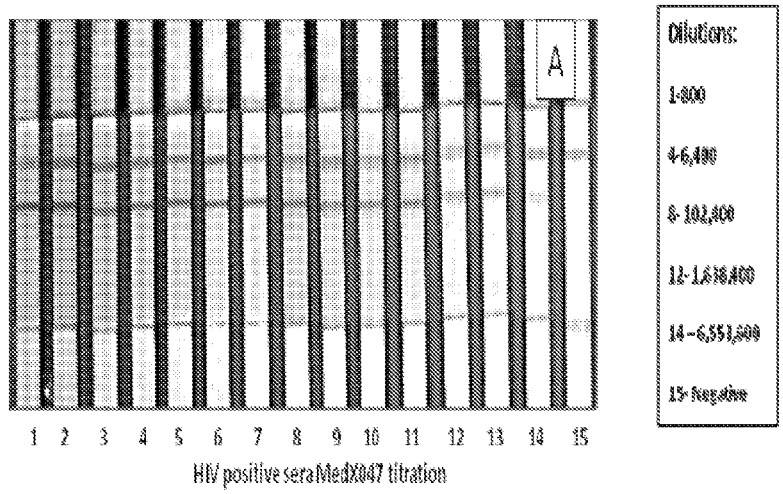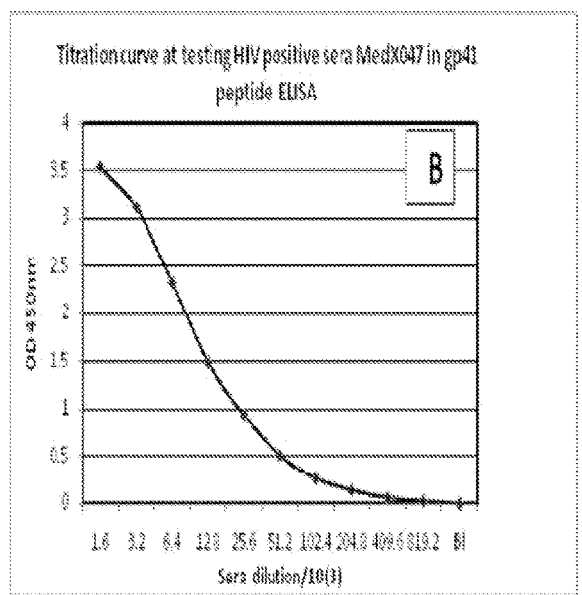
FIGURE 8. Comparison of detection limit at testing HIV positive sera in new lateral flow test (A) and ELISA (B)

COLOR-PRODUCING DIAGNOSTIC SYSTEMS, REAGENTS AND METHODS

RELATED APPLICATIONS

This application claims priority to U.S. Provisional Application Ser. No. 61/494,232, filed Jun. 7, 2011; the contents of which are hereby incorporated by reference.

BACKGROUND OF THE INVENTION

Rapid diagnostic tests all employ various principles of separation and detection of analytes on membranes. However, the vast majority of these tests use colorimetric labels with a fixed amount of optically active substances such as colloidal gold, non-metal colloids, pigment particles/polymers or liposomes loaded with dyes. Test results are usually read by visual analysis of color intensity in diagnostic zones. The use of simple portable scanners/densitometers was also implemented into diagnostic practices to reduce operator mistakes in data interpretation or to integrate point-of-care (POC) testing into database system. However, these detection methods have inherent limitations in sensitivity related to absorptive characteristics of these detector labels. The analytical sensitivity of rapid tests utilizing colorimetric labels is significantly lower than the sensitivity of plate enzyme-linked immunoassay (ELISA), which is currently the major method of clinical diagnostics widely applied to screenings or confirmatory tests for diagnosis of diseases or health conditions.

The emergence of new diagnostic markers requires more sensitive detection systems. Numerous methods were developed to increase the analytical sensitivity. Among them were methods utilizing various fluorescent labels, super-paramagnetic labels, and chemiluminescent approaches. However, most of these methods required sophisticated equipment for reading, such as fluorimeters or magnetic readers, not readily compatible with POC applications of these tests or accessible in low resource settings. The availability of stable colorimetric detection systems for rapid tests providing analytical sensitivity attained at clinical laboratories should significantly extend the area of application of rapid tests for cost-efficient diagnostics and other analytical applications.

Peroxidase, in particular horseradish peroxidase (HRP), is one of the most important enzymatic labels for detection of analytes by various methods, such as microplate enzyme immunoassay (EIA), Western blot, dot-blot, immunohistochemistry and electrobiosensors. Low cost, high activity, stability, compatibility with various biological matrices and the availability of very stable forms of commercial substrates all make this enzyme a very popular label for diagnostic tests and various bioanalytical applications.

Direct detection of peroxidative activity of certain diagnostic markers and research analytes is also an important application for peroxidase substrate systems. One example is detection of peroxidative activity of human hemoglobin as a marker for color cancer. Emerging markers with peroxidative activity, such as glutathione peroxidase and myeloperoxidase, are considered important prognostic markers for myocardium infarction and coronary artery disease. Many other peroxidases such as microperoxidases, eosinophile peroxidases, uterine peroxidases, lactoperoxidases, salivary peroxidases, thyroid peroxidases, prostaglandin H1/2 synthase and enzymes of oxidative stress (superoxide dismutase), are potential markers for various metabolic dysfunctions.

Peroxidase substrates, which are suitable for colorimetric, fluorescent and chemiluminescent analysis are commercially available (e.g. from Molecular Probes/Invitrogen, Pierce and AnaSpec). The broad spectrum of substrates available for immunohistochemistry allows for multicolor labeling. The most popular substrates for tests performed in microplates or tubes are TMB (3,3',5,5'-Tetramethyl-benzidine), DAB (3,3'-diaminodbenzidine), 1-Chloro-2-naphtol (CLN), diaminobenzidine, and ABTS (2,2'-Azinobis[3-ethylbenzothiazoline-6-sulfonic acid]-diammonium salt). U.S. Pat. No. 6,960,323 also describes various urea derivatives, which may be used as a peroxidase substrate.

The detection of a peroxidase labels in EIA tests is based on the oxidation of a substrate with peroxidase in the presence of a peroxide (e.g. hydrogen peroxide). This reaction generates soluble reaction products. Precipitating substrates are commonly used for the detection of a peroxidase label, which is bound to a membrane (Western blot, dot-blot, dip-strip tests). When a peroxidase substrate is reacted with a peroxidase in the presence of a peroxide, an insoluble colored reaction product is produced, which precipitates onto the membrane where the peroxidase is captured. Examples of this type of substrate include TMB, 4-chloro-1-naphtol and DAB. Methods which use combinations of two precipitating peroxidase substrates (CN/DAB, TMB/CLN) and enhancers of dye precipitation, such as metal ions (e.g. Ni and Co), have also been described.

However, TMB precipitating substrates do have some shortcoming. For example, the adsorption of oxidized TMB polymers on membranes depends on the type of molecule immobilized in the zones, which capture the enzyme label. In some cases, due to the high density of the reagents, the TMB polymers fail to stick efficiently. Moreover, high concentrations of captured enzyme labels can result in the formation of excessive precipitating reaction products can result in diffusion outside of the zone. It is also very common to see high background staining due to non-specific adsorption of the enzyme onto the membrane in areas outside of the diagnostic zones. Dyes formed by TMB polymers as well as with other precipitating HRP substrates (1-Chloro-2-naphtol, diaminobenzidine) are light sensitive and quickly fade even without being exposed to direct light. All of these drawbacks limit the applicability of TMB substrate systems for quantitative densitometric analysis. Also, TMB substrate can not be prepared in a dry form, which could be quickly reconstituted with an aqueous buffer.

HRP substrates producing light insensitive indamine type dyes as a complex of MBTH (3-methyl-2-benzothiazolinone hydrazone) with dienophile or an aromatic nucleophile is described in U.S. Pat. No. 5,432,285. Another HRP precipitating substrate system utilizes a combination of two reagents: 4-CN and MBTH or substituted p-phenylenediamine (Conyers, S M, Kidwell D A. Anal Biochem, 1991, 192: 207-211).

Oxidative coupling of 3-(dimethyl aniline)benzoic acid (hydrogen donor) with MBTH (3-methyl-2-benzothiazolinone hydrazone) (oxidizable coupling reagent) was described in Ngo et al (*Anal Biochem*, 1980, 105, 389-370). This method is similar to a method, which uses 4-aminoantipyrine as an oxidative coupler with a phenolic compound and aniline (Trinder, P., Ann. Clin. Biochem 6, 24-25 (1969)). In these methods, a hydrogen peroxide-oxidized form of HRP reacts first with an oxidizable compound (coupler), which then reacts quickly with a second compound (hydrogen donor) in a reaction of electrophilic substitution. The reaction proceeds without the participation of HRP to form strong chromophores, which are usually soluble compounds. This method was adapted for oxidative coupling of 3-(dimethyl aniline)benzoic acid with 3-methyl-2-benzothiazolinone hydrazone as a soluble substrate system for plate EIA tests (Georghegan et al, *J Immunol Methods,* 1983, 60, 61-68). These chromogenic systems produce intense colors that are relatively stable. However, the hydrogen donors used in these systems are unstable in solution. In addition, the sensitivity of this type of substrate for EIA assays is lower than the sensitivity of the best TMB HRP substrate.

Another method for detecting peroxidases, based on a two component dye system, was developed using leucodyes, which produce colors on membranes in the presence of an electron transfer reagent such as 4-hydroxyacetanilide (U.S. Pat. No. 5,024,935) and 3-aminopyrazolo heterocyclic derivatives in combination with aniline derivatives (U.S. Pat. No. 5,457,200).

A number of U.S. patents describe oxidative coupling of 4-aminoantipyrine or sulfoMBTH with various aniline derivatives including fluorinated derivatives (See e.g. U.S. Pat. Nos. 4,845,030 and 4,912,258).

Perhaps the most developed rapid diagnostics utilizing a two-component oxidative coupling dye system are enzymatic tests for the detection of low molecular weight substances such as glucose, cholesterol, uric acid, choline, alcohol, lactate, ascorbic acid, acetyl-CoA and certain drugs. In these systems, hydrogen peroxide is generated when the low molecular weight substance is oxidized with an appropriate enzyme (cholesterol oxidase, glucose oxidase, lactate oxidase, uricase, choline oxidase, ascorbate oxidase guanase, etc.). The hydrogen peroxide produced is then consumed by HRP, which uses a two component dye system to produce color. The amount of hydrogen peroxide produced correlates with the amount of the particular low molecular weight substance and the amount of dye generated by the HRP is based on the enzymatic conversion. The reagents for this substrate system may be distributed throughout the length of a diagnostic strip, so that the length of the colored zone on the diagnostic strip correlates quantitatively with the amount of test analyte in the sample.

Numerous patents describe two-component dye systems utilizing various hydrogen donor/coupler combinations for analyte detection in a strip format. The result may be visually read or read using a reflectance spectrophotomer or photometer (U.S. Pat. Nos. 6,858,401; 6,635,439; 6,531,322; 6,218,571; 5,972,294; 5,922,530 and 5,824,491). These tests typically require a liquid sample. Substrates that do not contain hydrogen peroxide are stable if prepared as a slowly soluble dry film or non-porous materials.

Several patents describe the use of hydrogen donors covalently immobilized onto a solid phase. For example, the quinoline type hydrogen donor, 8-(4-amino-1-methylbutylamino)-6-methoxyquinoline (primaquine) has been coupled to carbonyldiimidazole activated cellulosic membrane (U.S. Pat. No. 5,556,743) and used as part of a strip test for detecting cholesterol. A similar approach has been described for the immobilization of an aniline derivative with amino groups on CDI (carbonyldiimidazole) activated cellulose membrane (U.S. Pat. No. 5,155,025). Aniline derivatives with primary amino groups such as N-alkyl 3-oxyanilines were synthesized as insoluble polyvinyl alcohol polymer conjugates (U.S. Pat. No. 5,409,780). Such insoluble polymers were applied as plastic films and used as a rapid test for testing glucose in blood or urine.

Various patents also describe various oxidative couplers (e.g. MBTH, 4-aminoantipyrine, analogs of 4-aminoantipyrine, a modified MBTH with increased solubility, which contains a carboxyl group (U.S. Pat. No. 5,710,012); a salt of 6-carboxy-3-methylbenzenothiazolene hydrazone hydrate; MBTH derivatives that are sulfonated on the ring (U.S. Pat. No. 6,242,207); 3-methyl-6(sulfonate salt)-benzothiazolinone-(2)-hydrazone) or an N-sulfonyl benzensulfonate derivative (U.S. Pat. No. 5,992,530); meta[3-methyl 2-benzothiazolinone hydrazone]N-sulfonyl benzenesulfonate monosodium) or as dinitrobenzene derivatives (U.S. Pat. No. 4,962,040) and 2-hydrazono-4,6,-dinitrobenzthiazolone). Other combinations of hydrogen donor/couplers for the determination of peroxidatively active catalysts such as amino benzidine type hydrogen donors and substituted phenol type couplers are described in U.S. Pat. No. 5,532,138.

The vast majority of currently available membrane-based immunodiagnostic tests that utilize peroxidase and another enzyme label, use principles of vertical filtration (flow through), dip-sticks and other formats, which rely on passive diffusion. The basic components of flow-through rapid diagnostic kits are liquid reagents, HRP conjugates, HRP substrates and a wash buffer. A precipitating substrate system (usually a TMB based substrate) is typically used to detect the peroxidase activity of a bound enzyme.

Lateral flow (LF) rapid tests with enzyme detector labels, which generate dyes, currently represent a very small segment of the diagnostic market. The advantages of using highly sensitive enzyme labels are difficult to obtain in simple LF rapid tests, which utilize only dry components. Enzyme labels require an additional component, the substrate, and in most cases require a more efficient washing step, which imposes additional challenges and costs.

Certain patents describe lateral flow devices, which utilize liquid or dry HRP conjugates and liquid TMB precipitating substrates integrated into diagnostic cassettes as a sealed container together with a container of wash buffer. These containers can be perforated to initiate the flow of wash buffer and subsequent delivery of substrate into the diagnostic zones on a fast flow porous polyethylene matrix (U.S. Pat. Nos. 7,442,557; 6,436,722 and 5,726,010). Positive results can typically be measured visually after about 8-10 minutes.

Certain patents describe LF strips with dual paths, one for the delivery of any enzyme labeled analyte, and the other for the delivery of reconstituted substrates for alkaline phosphatase or beta-galactosidase based systems) with appropriate washing separating these two processes (U.S. Pat. No. 6,706,539). Other patents describe devices, which contain zones of immobilized substrates. These zones generate color when an enzyme enters by diffusion through a permeable barrier (U.S. Pat. No. 4,806,312). Lipid vesicles (e.g. liposomes) loaded with enzyme substrates may also be captured into a test zone. In the presence of a specific analyte and enzyme label, the vesicles can release the enzyme substrate into the test zones with the aid of a phospholipase, which has been incorporated into a capture zone.

Commercially available dip-strip tests utilize porous or non-porous materials to immobilize capture reagents, liquid enzyme conjugates and substrate reagents. The whole strip or a working portion may be incubated in a series of solutions (e.g. sample, conjugate, washing solution and substrate).

The use of HRP as a label for conventional LF tests faces other technical challenges. Among the most critical is the absence of stable dry forms of peroxidase substrates containing a peroxide compound. Also many peroxidase substrates, such as TMB, are not very soluble. And although special additives may be used to maintain TMB in solution, these mixtures cannot be prepared in an appropriate dry form suitable for quick solubilization (See U.S. Pat. No. 5,910,423). Other peroxidase substrates, which produce precipitating products require organic solvents to maintain their solubility, some of which are carcinogenic. Glucose oxidase co-immobilized with capture antibodies on membranes can produce hydrogen peroxide for HRP chromogenic reactions in the presence of glucose. This approach was applied for quantitative analysis of low-molecular weight analytes in competitive tests where the length of the colored zone on the strip is a measure of the analyte concentration (Li et al. Analyt Biochem, 1987, 166, 276-83, Zuk et al. Clin Chem, 1985, 7, 1144-50). However, this approach has limited analytical sensitivity.

All of the currently available substrate systems for peroxidase produce a monochromic color, due to the precipitation of a common dye polymer. The internal control zones and test zones on these membranes typically only generate a color in the violet-blue range.

Accordingly, there is a need for more sensitive peroxidase substrate based rapid tests, which employ stable dry reagents.

SUMMARY OF INVENTION

Described herein are new highly sensitive and stable multicolor substrate systems for the detection of peroxidases or peroxidatively active substances. Peroxidases and peroxidatively active substances, for example, can be: a) detector labels in various assays for the detection of analytes, b) part of an enzymatic cascade utilizing peroxides produced from conversion of an analyte, or c) themselves analytes or diagnostic markers.

The systems rely on known principles of two-component dye systems, where dye formation is the result of oxidative coupling between compounds, which are known as hydrogen donors with electron acceptors/couplers. These couplers are oxidized with a peroxide in the presence of a peroxidase or a peroxidatively active substance.

Also described herein are new stabilized forms of hydrogen donors, referred to herein as "hydrogen donor conjugates," which may be incorporated into various zones of a diagnostic membrane. Reaction between a hydrogen donor conjugate and an oxidized coupler in the presence of a peroxidase or peroxidatively active substance will produce a particular color depending upon the chemical nature of the particular hydrogen donor conjugate. Use of a plurality of different hydrogen donor conjugates incorporated into diagnostic zones on membranes allows for the detection of several analytes in multiplexed rapid tests producing specific color for each test analyte, which can be easily discriminated by the naked eye or with the assistance of a spectrophotometer.

Hydrogen donor conjugates may be comprised of a hydrogen donor compound covalently linked to a hydrophilic material. The hydrogen donor compound for synthesis of hydrogen donor conjugates may be an amine containing compound, for example, an aniline, quinoline, naphtole or phenol, which is suitable for covalent coupling, including, for example, 8-[4-amino-1-methylbutyl]-6-methoxy quinoline (PQ), N,N-[dimethyl-1,3-phenylenediamine dihydrochloride (DMPA), N-(1-naphthyl)ethylenediamine dihydrochloride (NED), and N-phenylethylenediamine (PEDA).

The hydrophilic material can be a carboxyl containing compound, such as a carboxylic polymer, a carboxyl containing protein (e.g. a serum albumin or a serum albumin derivative) or a carboxylate particle (e.g. a carboxylate modified latex (CML) particle). In certain embodiments, the carboxylic polymer is a linear polymer (e.g. polyglutamic acid, polyaspartic acid, polyacrylic acid, polymaleic acid, polymethacrylic acid, polyacrylamide/polyacrylic acid copolymer, polyvinyl-maleic acid copolymer, polyacrylamide-polyethylene maleic acid copolymer and polyacrylic-polymaleic acid copolymer. The carboxylic compound can also be a branched oligomer, such as ethylenediamine tetraacetic acid (EDTA) or ethylene glycol-bis(2-aminoethyl-ether)-N,N,N',N'-tetraacetic (EGTA) and dendrimers with multiple carboxyl groups.

Preferred hydrogen donor conjugates are comprised of amine hydrogen donors conjugated with a polymeric backbone, such as a polycarboxylic polymer or protein-polycarboxylic polymer. Conjugates may be additionally hydrophilized by incorporation of polyethylene glycol (PEG). These hydrophilized hydrogen donor conjugates contain multiple copies of hydrogen donors and are easily solubilized in aqueous solutions. These donors can generate, in a reaction of oxidative coupling, dyes with various colors, having absorbance maximum in a range of 450-650 nm (i.e. red, rose, light blue, dark blue, and various gradations of violet). Additional color pallets can be obtained by mixing various hydrogen donors at synthesis, or by mixing hydrogen donor polymer conjugates of different hydrogen donors.

Hydrogen donor conjugates may also contain a member of a high affinity binding pair (biotin as the most common example or also an antigen (of an antigen/antibody pair), antibody (of a antibody/antigen pair), nucleic acid (for example a single strand nucleic acid, which is able to hybridize with a complementary single strand nucleic acid) or conjugates thereof). Hydrogen donor conjugates, which further include a member of a high affinity binding pair may be used to capture analytes in a diagnostic tests or for signal amplification. Alternatively, a hydrogen donor conjugate may be mixed with a specific analyte capture reagents (antibody, antigen, nucleic acids or conjugates thereof) and applied together on membranes for formation of test and control zones.

Hydrogen donor conjugates may further contain various functional groups (e.g. carboxyl or amino), which allow for their covalent immobilization onto various carriers, such as membranes, non-porous solid phase and particles, or for conjugation with other soluble reagents.

Water soluble hydrogen donor conjugates containing hydrogen donors, polymers and protein carriers have high binding affinity to various membranes suitable for passive adsorption such as nitrocellulose, nylon, pure glass fiber membranes or non-porous active solid phase materials.

Hydrogen donor polymer conjugates can be applied on membranes alone or as a mixture with other reagents such as antibodies, antigens or specific binding partners, to make test and control zones on diagnostic membranes. After adsorption on membranes, hydrogen donor conjugates produce zones that are invisible on a white membrane background.

The amount of hydrogen donor conjugates required to generate strong color in diagnostic zones is in most cases much lower than the saturating concentration for membranes allowing for the mixing of hydrogen donor conjugates and other reagents without compromising sensitivity.

Hydrogen donor conjugates, as described herein, are very stabile. Aqueous solutions of these hydrogen donor conjugates are suitable for long term storage. Moreover, most of hydrogen donor conjugates can be freeze-dried, and the resulting dry reagents can be dissolved in water to form clear solutions. These hydrogen donor conjugates are very stable when dried onto membranes and can be stored for years in the presence of desiccants without a visible reduction in dye formation.

Hydrogen donor conjugates may be prepared in particle-bound form, which can be used for making diagnostic zones based on being trapped into membrane pores or may be used in filtration assays.

Also described herein are several methods for loading hydrogen donor conjugates (with or without the addition of a member of a high affinity binding pair) onto particles. In one method, soluble hydrogen donor conjugates are immobilized on polystyrene latex particles through passive adsorption. In a second method, soluble hydrogen donor conjugates are covalently coupled via amino or carboxyl groups to particles, which contain an appropriate reactive group. In a third method, covalent immobilization of hydrogen donor conjugates on particles together with PEG is described. In a fourth method, immobilization of hydrogen donor conjugates on particles, which are subsequently loaded with protein and polycarboxylic polymers to further increase the density of carboxylic groups and hydrophilicity is described.

Particles loaded with hydrogen donor conjugates and hydrophilizing polymers and/or proteins produce stable suspensions without a visible tendency for flocculation or formation of aggregates. Particles loaded with hydrogen donor conjugates can be mixed with particles, which containing a reagent, which may selectively bind with an analyte (e.g. an antigen, antibody or nucleic acid) and applied together onto a variety of diagnostic membranes such as glass fiber, glass fiber with binder or porous polyethylene. Particles incorporated into high pore membranes withhold fast liquid flow and can be used in rapid diagnostic or analytical tests to provide a highly sensitive readout in a very short amount of time. The use of white particles produce practically invisible zones when incorporated onto a membrane. These particles can generate strong, bright colors in diagnostic zones on membranes. The particles can also be used as suspensions in bead filtration assays.

Another novel aspect of the described detection system is its unique potential for application in multiplexed tests with several control and diagnostic zones on analytical membranes. The reaction of an oxidized coupler with a hydrogen donor conjugate immobilized on a membrane produces a bright dye strictly in zones with an immobilized hydrogen donor conjugate. A membrane may be prepared to contain several test zones or control zones, each zone containing a particular hydrogen donor conjugate or mixture of hydrogen donor conjugates, each generating a different color as an indication of a different analyte. Assays, which employ immobilized hydrogen donor conjugates are absolutely free from background staining, which happens frequently with conventional precipitating peroxidase substrates.

The reaction, which results in dye formation may be stopped by assay wash buffer or by using one of various stop reagents, which effect enzyme activity, block the oxidative coupling reaction, or both. Stop reagents do not produce a color change of the reaction products. Dyes produced in solution or on membranes using soluble hydrogen donor conjugates or particles are not light sensitive. Diagnostic membranes preserve color after drying and can be stored for a long time with only minor fading and without requiring any special means for protection against light, thus facilitating data interpretation and analysis.

Soluble polymeric hydrogen donor conjugates produce dyes with a higher molar absorbance than is obtained with non-conjugated hydrogen donors. The colored reaction products in most cases are also soluble, which allows soluble hydrogen donor conjugates to be used in plate-based assays.

Also described herein are stable peroxidase substrates comprised of MBTH or an MBTH derivative and sodium perborate. MBTH and MBTH derivatives, which provide maximum analytical sensitivity in oxidative coupling reactions with immobilized hydrogen donors. Certain substrates may be optimized for use as a stable liquid reagent. Another reagent may be suitable for drying (using elevated temperature, in vacuum or freeze drying process), including on porous materials. Coupler/peroxide reagent dried on porous materials can be quickly reconstituted with assay wash buffer providing efficacy similar to the original liquid form. The sensitivity provided by the described peroxidase substrates may be further increased by adding an enhancer/accelerator of dye formation such as acetaminophen.

The versatility of this new substrate system was demonstrated by developing a variety of rapid diagnostic tests, as further described herein. For example, certain assays utilize lateral flow, dip-strip, flow through or passive diffusion formats for the detection of antigens and antibodies, and direct detection of analytes with peroxidative activity, such as hemoglobin. A comparison of the sensitivity of the tests described herein with that of similar rapid tests, which use a conventional label (e.g. colloidal gold), demonstrate at least two orders of magnitude higher sensitivity for the new tests. In addition, the new tests require less time to complete due to the very fast kinetics of dye formation. Due to the high sensitivity, new tests based on lateral flow principles can effectively use fast flow diagnostic membranes. Assay time in some cases can be reduced to 2-3 minutes. Flow through tests require even less time. In most cases, highly sensitive rapid tests in lateral flow or flow through formats can be realized in 5-8 minutes. A direct comparison of the sensitivity of new rapid tests with the sensitivity of optimized plate based ELISA, which use the same capture and detector enzyme conjugates, demonstrate that the instantly disclosed substrate system is more sensitive, sometimes by an order of magnitude. The sensitivity of the substrate system described herein also exceeds the sensitivity of the best precipitating TMB-based HRP substrates. In addition, assays, which employ the substrate systems described herein do not undergo non-enzymatic side reactions, which could result in a non-specific signal.

Rapid tests in the lateral flow format are sensitive enough to detect 10-15 pg of antigen per ml. Some bacterial antigens can be detected in a sample containing 10-20 cells per strip. The sensitivity of antibody detection is in the range 10-15 pg per strip. As a detector label, HRP can be detected in amounts as low as about 0.1 pg/strip.

Water soluble hydrogen donor conjugates and particles loaded with hydrogen donor conjugates do not result in non-specific binding of enzyme labeled reagents and will not produce false-positive results, if appropriate wash steps are followed. In addition, negative results stay negative for a long time after tests are completed, thus eliminating the need to immediately read results.

Because dye is generated exclusively in diagnostic zones, which contain immobilized hydrogen donor conjugates, and there is no background staining or diffusion of dyes outside of the diagnostic zones, the new substrate system also provides a quantitative rapid test, which relies on a simple densitometric analysis of the kinetics of dye formation in the diagnostic zone.

Further features and advantages of the assays and reagents described herein will be apparent from the following Detailed Description and Claims.

BRIEF DESCRIPTION OF DRAWINGS

FIG. 3 shows results of simple flow through tests for detection of anti peptide antibodies and antigen utilizing particle-bound hydrogen donors and analyte capture reagents spotted on Fusion 5 glass fiber membranes (3A) or porous polyethylene matrix (3B). The test for detection of antibodies against C6 Lyme peptide easily detected antibodies in medium titer Lyme positive sera at dilutions exceeding 1000 times in about 2 minutes time. The membrane contained two test zones with C6 peptides and different hydrogen donors generating blue and violet dyes. Membranes for the heartworm antigen test also contained three antigen capture test zones generating blue, violet and rose dyes with a red internal positive control spot.

FIG. 5 shows the results of a lateral flow/dip-strip test on Fusion 5 for the detection of antibodies against cysticercosis antigen T24 using serial dilution of one positive sample (A) in comparison with testing for the same antigen using a plate ELISA (B). Test lines contained particle-bound hydrogen donor conjugates of DMPA and biotin. Positive control lines contained particle-bound PQ and anti-HRP antibodies. Antibodies were captured in the test lines as complexes with two antigen conjugates: T24-StrAv and T24-HRP. The same T24 conjugates and biotin-BSA coated plates were used for ELISA testing (FIG. 5 B). The LF/dip strip test on Fusion 5 with an assay time of 6-8 minutes detected antibodies against T24 antigen at dilutions of at least 20,480 fold compared to only 12,800 fold in the QuickELISA.

FIG. 8 shows the results of a comparison of the sensitivity of lateral flow tests for the detection of antibodies against the HIV gp41 peptide (FIG. 8A) and a corresponding ELISA test utilizing the same peptide conjugate and detection formats (FIG. 8B). Test and control lines contained soluble NED and PQ hydrogen donor conjugates striped on the nitrocellulose membrane CN-95. The test line with NED contained biotin and PQ control line anti-HRP IgG. Serially diluted samples of HIV positive sera were combined with conjugate mixtures containing the gp41 peptide. -StrAv and anti-human-IgG-HRP and 10 µl sample/conjugate mixture were added on the sample pad zone on the diagnostic strips. Washed strips were developed with 15 µl MBTH/perborate substrate. Total assay time was approximately 8 minutes. The positive control line produced a red color, the test line a bright blue color. The new lateral flow test detected antibody in high titer HIV positive sera at dilutions exceeding 6 million (FIG. 8A), whereas the ELISA test with a similar antibody detection format detected antibodies in the same sera only at dilutions up to 400,000 (FIG. 8B)

DETAILED DESCRIPTION OF THE INVENTION

1. General

Figure 1:
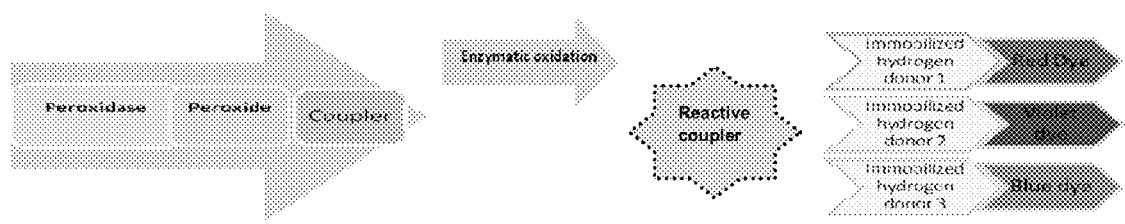
FIG. 1 is a schematic representation of how color is formed utilizing immobilized hydrogen donor conjugates. An oxidizable coupling reagent in the presence of peroxide and peroxidase reacts with various immobilized hydrogen donor conjugates to produce various colors depending on the type of immobilized hydrogen donor.

Described herein are reagents of two component substrate systems for peroxidative enzymes based on hydrogen donor conjugates and stabilized couplers. Combinations of one coupler and different hydrogen donor conjugates produce a spectrum of different colors in a reaction of oxidative coupling in the presence of peroxidase enzyme or a peroxidatively active substance and a peroxide compound (FIG. 1). These stable reagents can be applied on test zones of membranes to make various rapid membrane-based tests. In such tests, multicolor results can be obtained, whereby test zones for one or several analytes and internal control zones have specific colors significantly simplifying visual reading.

Hydrogen donor conjugates are preferably stable, water soluble and/or may be easily adsorbed onto or covalently coupled to membranes or particles. Hydrogen donor conjugates may also contain analyte-binding reagent or component of a high affinity binding pair, which may participate in the specific binding of test analyte. Alternatively hydrogen donor conjugates may be mixed with specific analyte-capture reagents and applied together on membranes.

Hydrogen donor conjugates may be incorporated into a variety of assay formats such as lateral flow, flow-through, dip-strip, passive diffusion, dot-blot, microarray and bead-filtration for detection of various analytes, utilizing principles of enzyme immunoassay, nucleic acid detection, direct detection of analytes with peroxidative activity and analysis of analytes generating peroxides under enzymatic conversion.

2. Reagents of the Multicolor Substrate System

Numerous compounds with potential hydrogen donor activity such as anilines, quinolines, naphtoles, naphalenes, phenols, and benzoic acid derivatives are currently commercially available. Among the commercially available compounds are those with primary amino groups, carboxyl groups and hydroxyl groups, which are suitable for covalent coupling using any of a variety of conjugation chemistries. Most hydrogen donors are relatively hydrophobic and some have limited solubility in aqueous buffers.

Amine-containing hydrogen donors may be the most suitable compounds for synthesis of hydrogen donor conjugates due to the plurality of hydrophilic soluble polycarboxylic polymers currently available and high efficacy and simplicity of conjugation methods utilizing water-soluble carbodiimide chemistry.

Conjugation using water-soluble carbodiimide (EDAC) in combination with N-hydroxysuccinimide, sulfo-N-hydroxysuccinimide or N-hydroxybenzotriazole may be the most convenient method for coupling of amino-containing compounds to carboxylic functional groups and it can be accomplished with good yield in aqueous buffers with minimal and simple purification of the final product. For example, conjugates synthesized in aqueous buffer may be simply purified by dialysis, hollow fiber filtration or gel-permeation chromatography.

Extensive screening of various compounds that have primary amino, carboxyl or hydroxyl groups (e.g. anilines, quinolines, naptholes, phenols, halogenated phenols, benzoic acid derivatives) suitable for covalent coupling with polymers was carried out. As a result, many compounds were selected which showed the ability to participate in oxidative coupling with a MBTH type coupler or other types of couplers following covalent immobilization on polycarboxylic polymers such as polyacrylic acid, polymaleic acid and their co-polymers with polyacrylamide or polyethylene, poly-glutamic and poly-aspartic acids. Most dyes formed in the reaction of oxidative coupling with MBTH coupler have absorbance maxima in the range 490-650 nm. Some MBTH derivatives can also be used as efficient couplers in reactions with hydrogen donor conjugates. Such MBTH derivatives include, but are not limited to, the salt of 6-carboxy-3-methylbenzothiazolone hydrazone hydrate (U.S. Pat. No. 5,710,012), the salt of 3-methyl-6-sulfonyl-2-benzothiazolinone hydrazone (U.S. Pat. No. 6,379,915), and the salt of meta [3-methyl 2-benxothiazolinone hydrazone]N-sulfonyl-2-benzensulfonate (U.S. Pat. No. 5,563,031).

Hydrogen donors that generate dyes with high absorbency include: 8-[4-amino-1-methylbutyl]-6-methoxy quinoline (Primaquine, PQ), 6-amino-quinoline, 8-amino-quinoline, N,N-[Dimethyl-1,3-phenylenediamine dihydrochloride (DMPA), N-(1-Naphthyl) ethylenediamine dihydrochloride (NED), and N-Phenylethylenediamine (PEDA). This list may be extended to include certain derivatives of the compounds listed above and through additional search of reagents. Appropriate hydrogen donors must not be able to participate in direct oxidation with peroxide in the presence of peroxidase. Although, some compounds that are weak substrates for peroxidases may also be suitable hydrogen donors. Also, compounds such as N-phenylethylenediamine, which is a very weak hydrogen donor in non-conjugated form, may become relatively active after becoming conjugated, for example to polycarboxylic polymers.

Numerous compounds working as efficient hydrogen donors in a free form and containing carboxylic groups and hydroxyl groups, (examples are 3-(Dimethylamino)benzoic acid, 2,3,4-trihydroxybenzoic acid and 2,4,6-Tribromo-3-hydroxybenzoic acid) chroomotropic acid) were found to almost completely lose activity as donors when reacted with oxidized couplers after having been covalently coupled to amino-containing polymers (poly-allilamine, poly-vinylamine, poly-lysine) or amino-modified latex particles using water soluble carbodiimide, vinyl benzene or epoxide conjugation chemistries.

In addition to the hydrogen donors and conjugation chemistries described above and in the following examples, one of skill in the art may using only routine experimentation arrive at other hydrogen donor conjugates and different conjugation chemistries. Conjugation of the most active hydrogen donor compounds containing primary amino groups with polycarboxylic polymers at high density may produce hydrogen donor conjugates with limited solubility in aqueous buffers. These conjugates may form high molecular weight aggregates or viscous colloid-like substances. During oxidative coupling, the solubility of such hydrogen donor conjugates may be further reduced, thereby producing strongly insoluble dye aggregates.

It is important for hydrogen donor conjugates to be water-soluble. By being water soluble, hydrogen donor conjugates may be easily adsorbed onto membranes or particles, They are also stable during storage and may be freeze-dried and reconstituted in water or buffers as clear solutions.

The solubility of hydrogen donor conjugates may be enhanced, for example, by adding various combinations of proteins, such as bovine serum albumin (BSA); polycarboxylic oligomers and polymers, and hydrophilic polyethylene glycol (PEG) polymers.

Pegylation is well-known as an efficient method for increasing the solubility of various substances and is used in numerous areas of bioconjugation (Polyethylene glycol chemistry: biotechnical and biomedical applications, edited by J. Milton Harris, Plenum Press, 1992). Abroad spectrum of PEG-based reagents with various functional groups are available, such as: mono-functional (primary amine, carboxylic thiol, aldehyde), bi-functional cross-linking PEG, amino-functional, activated PEG for reaction with amines, thiols, hydroxyl groups as well as branched PEG and PEG with biotin, activated with maleimide, succinimide or with primary amino groups, as well as PEG with BOC protection. (Lysan Bio, Nanocs, Sigma-Aldrich, PolySciences, Thermo-Scientific).

Numerous water soluble hydrophilic polycarboxylic polymers such as polyacrylic acid, polymethacrylic acid, polymaleic acid, copolymers of polyacrylic-maleic acid, polyacrylic acid-polyacrylamide, poly-glutamic acid, poly-aspartic acid and poly acrylic/maleic anhydrides, compounds with a small number of carboxylic groups 4-16 are currently available from various commercial sources (Sigma-Aldrich, Poly-Sciences).

Also described are use of polycarboxylic polymers representing polyacrylic acid of various molecular weights (MW in a range 1,000-345,000 Da) and copolymers such as polyacrylic acid-acrylamide, polymetacrylic acid, polyvinyl-maleic acid, polymaleic acid, poly-glutamic acid, poly-aspartic acid and polycarboxylic compound for covalent coupling of hydrogen donors containing primary amino groups. To enhance solubility in aqueous buffers, covalent coupling of hydrogen donors proceeds in a mixture with amine-PEG polymers at an appropriate ratio of amine-hydrogen donor/ amine PEG. Amine-PEG can be used as biotin-PEG-amine for coupling with polycarboxylic polymers simultaneously with amine-donors. By varying the ratio between amine hydrogen donor and amine PEG in a mixture, the degree of hydrophilization of polymer conjugates may be controlled. Varying the molecular mass of PEG may also impact the degree of hydrophilization of the final conjugates. Amine-PEG, or amine-PEG-Biotin are preferred compounds with MW between 1K and 20K (1K, 2K, 3.4K, 5K, 10K, 20K). The resulting hydrogen donor conjugates may contain additional bioaffinity groups, such as biotin, which can be effectively used for analyte capture in numerous assay formats. Bioaffinity groups can be selected from numerous compounds representing low molecular weight substances such as peptides or nucleic acid probes. Hydrogen donors may be loaded with bioaffinity groups at the same time as PEG polymers are added. The resulting hydrogen donor conjugate may be purified by simple dialysis and then may be adsorbed on membranes or particles.

Polycarboxylic polymers may first be react with a protein such as BSA, which may be additionally hydrophilized through modification with PEG. For example, BSA may be modified through amino groups using amino-reactive PEG derivatives. Amino-PEG may also be hydrophilized through the carboxyl groups of BSA using water soluble carbodiimide in conditions that minimize cross-linking between BSA molecules. Both approaches provide essential hydrophilization of BSA to maintain water solubility after loading with polymers and hydrogen donors.

Amino-reactive PEG derivatives suitable for BSA pegylation, include p-nitrophenyl carbonate PEG (MW 5 kDa and 10 kDa as examples) and various succinimidyl ethers of PEG with MW 2-20 kDa. Other amino-reactive PEG derivatives can be used for this purpose. Typically, modification of 4-6 amino groups in BSA with PEG (out of a total of 10-12 surface amino groups available for modification) hydrophilizes BSA, while preserving the amino groups for coupling with poly-carboxylic polymers. The presence of pegylated BSA also significantly reduces cross-linking when reacted with activated of carboxyl groups. BSA-PEG may be loaded with polycarboxylic polymers, the latter should be activated with EDAC/NHS in a manner which allows only partial activation (10-15% of available carboxylic groups in polycarboxylic polymer solution). This helps to prevent cross-linking of BSA-PEG upon reaction with an activated polycarboxylic polymer. The coupling of amine hydrogen donors at the next step proceeds through reaction with carboxyl groups on conjugated polycarboxylic polymers and BSA. Covalent coupling of amine hydrogen donors in a mixture with amine-PEG provides maximum hydrophilization and produces conjugates that can be freeze-dried without loss of solubility. Simple and efficient dialysis procedures (dialysis membrane or hollow fiber cartridges with large pore sizes, ~25-50 kDa) may be used to purify the conjugation products from non-conjugated polymers.

Hydrogen donors conjugates synthesized using PEG-modified, BSA carrier have a higher binding affinity for nitrocellulose membranes and are better at being passively adsorbed onto polystyrene particles than polycarboxylic acid conjugates.

Carboxyl groups may also be added onto BSA-PEG for coupling with amine donors using polycarboxylic compounds which have a small, fixed number of carboxyl groups, such as the known tetraacetate chelates EDTA, EGTA or similar branched compounds containing 4, 8 or 16 (pendant) carboxyl groups (e.g. PAPAM dendrimers from Sigma). Similar to linear polyacetic acid polymers, activation of these oligomers for coupling with BSA-PEG preferably should be limited to 1-2 available carboxyl groups. Despite the lower density of hydrogen donors in this type of conjugate, they bind to membranes with high affinity and provide relatively high density of dyes when reacted with oxidized coupler. Alternatively, carboxyl groups may be added into BSA-PEG using reactions with poly-anhydrides such as polymaleic anhydride or copolymer of maleic anhydride-polyethylene.

Many other reagents may be used for making hydrophilic poly-carboxylic constructs suitable for coupling with amine hydrogen donors and forming water soluble hydrogen donor conjugates, provided that they provide the necessary balance between hydrophilic and hydrophobic portions and do not create non-specific binding of the detection reagents in diagnostic tests or induce non-enzymatic oxidation of the hydrogen donors.

Water soluble hydrogen donor conjugates produced by the methods described above are clear with only a minor residual orange pigmentation for the PQ conjugates. After adsorption on white membranes, these reagents become practically invisible. Solutions of hydrogen donor conjugates can be stored for months in buffers containing EDTA without any visible accumulation of oxidation products or reduction in activity. Reagents dried on membranes may be stored at room temperature for years without loss of activity.

Upon reaction with an oxidative coupling agent, such as MBTH, most hydrogen donor conjugates produce soluble dyes. This property allows these reagents to be used as stable substrates for plate-based assays.

Soluble polymer conjugates have a high density of hydrogen donors that provide a very strong color after being adsorbed onto membranes at concentration even significantly below the binding capacity of the membrane. For example, to produce a strong visible signal, BSA-PEG-Poly Glu-Donor-PEG conjugates, can be applied onto nitrocellulose type membranes at a concentration of 0.1-0.2 mg/ml at a rate of 1 ul/cm (0.05-0.1 ug per 5-mm strip), which is at least 10 times below saturating concentration for the membrane. A working concentration for striping these conjugates on a nitrocellulose membrane is in the range of 0.5-0.8 mg/ml. Soluble hydrogen donors can be used for making test zones on microarray slides through passive adsorption or by covalent linking to an amino reactive surface. Most of soluble hydrogen donor conjugates can be passively adsorbed on pure glass fiber membranes, and some on glass fiber membranes with binder. These hydrogen donor conjugates can be mixed with other proteins (antigens, antibodies, special conjugates) necessary for creation of analyte capture systems and applied together on membranes which provide zones with a high binding capacity for the test analytes and an ability to generate strongly colored zones after being captured by a peroxide or an analyte with peroxidative activity.

Hydrogen donors containing amino and carboxyl groups may be coupled with appropriate particles, which contain carboxyl groups, activated amino-reactive groups or amino groups. A large selection of carboxylic and amine modified particles are commercially available. Preferred particles have a high density of carboxyl groups such as CML particles (Invitrogen, Thermo Scientific). CML particles loaded with hydrogen donors maintain mono-dispersity, and do not flocculate or produce aggregates, which could be difficult to resuspend.

Several approaches are available for making particles loaded with hydrogen donors. In one method, amine donors are directly coupled with carboxylate particles, preferably together with mono-amine-PEG or amine-PEG-Biotin so that the particles are stable in suspension. Another method utilizes passive adsorption of BSA-PEG-poly carboxylic acid donors-PEG conjugates on polystyrene particles. In a further method, particles are loaded with BSA through covalent coupling with carboxyl groups and further loaded covalently with additional polycarboxylic polymers and then with amine-hydrogen donor/PEG. This type of particle has a very minimal tendency to flocculate and is easy to resuspend. Yet another method uses CML particles and the soluble hydrogen donors are covalently attached to the carboxyl groups of particles.

Hydrogen donors immobilized on particles (preferably in a range of 0.4-2 uM size) can be simply incorporated into high pore membranes as dots or lines which also contains a component of a specific capture system for analytes e.g. (antibodies, antigens, components of high affinity binding pairs). Glass fiber type membranes, e.g. Fusion 5 (Whatman/GE Healthcare) developed for application in lateral flow tests is a good membrane for receiving particles. Many glass fiber membranes can also be used for passive diffusion types of assays. Particles with hydrogen donors may be applied on membranes in buffers alone or mixed with immunoassay stabilizers or additional detergents. Particles may be applied using an airjet-type of dispenser. Particles with immobilized hydrogen donors may be easily incorporated into hydrophilic porous polyethylene matrix with pore sizes of 10-50 uM (Porex) as spots or lines. Particles associate with a porous matrix, strongly withhold vertical or horizontal flow of various liquids through a matrix (including solutions with high protein and detergent content) without becoming dissociated. Particles are white and after becoming incorporated produce zones, which are practically invisible on white membrane backgrounds. Particles loaded with hydrogen donor conjugates may be used in bead filtration assays to generate an easily read signal in filter plate wells.

The high density of hydrogen donors in hydrogen donor conjugates or on particles significantly increases the reaction kinetics with oxidized couplers, which are produced in the proximity of hydrogen donors by specifically captured HRP labels or another peroxidative enzyme. Thus, the sensitivity is significantly increased in comparison with a reaction in solution.

Contrary to most conventional HRP substrates, the dyes produced from hydrogen donor conjugates and a coupler are not light sensitive. As a result, developed membranes may be stored for many days after the reaction is stopped and membrane dried. The presence of hydrogen donor conjugates only in zones where they are applied prevents background staining and formation of diffusion products. The dyes have a bright color and are easily discriminated by the naked eye. The amount of hydrogen donor, which may be incorporated into zones on membranes is enough to produce a strong signal. An analysis of the kinetics of dye formation can be done precisely measured using an appropriate densitometer, thereby quantifying the analyte.

3. Use of Hydrogen Donor Conjugates in Rapid Diagnostic Tests

Hydrogen donors conjugates may be used in a variety of rapid test formats that utilize HRP as a detector label. One format, which was the first adapted for use of an enzyme label, is the flow-through format, also known as a vertical filtration or an immunoconcentration test. Flow through are typically used to detect antigens or antibodies.

Two different hydrogen donor conjugates: one using soluble BSA-PEG-donor-PEG-PEG-Bi-conjugates and the other immobilized particle, were used for making test and control zones on membranes. Analyte capture reagents such as antigens (peptides, recombinant antigens) or antibodies were co-immobilized with hydrogen donor conjugates in corresponding test zones as spots or lines, dashed lines or a combination of differently shaped zones on a diagnostic membranes. All major types of membranes that adsorb reagents by physical adsorption appears to work with the hydrogen donor reagents. High pore nitrocellulose with or without paper backing appears to work particularly well for this purpose. Some pure glass fiber membranes (e.g. Ahlstrom 111) also adsorb soluble reagents strongly enough for use in flow-through tests.

Figure 2:
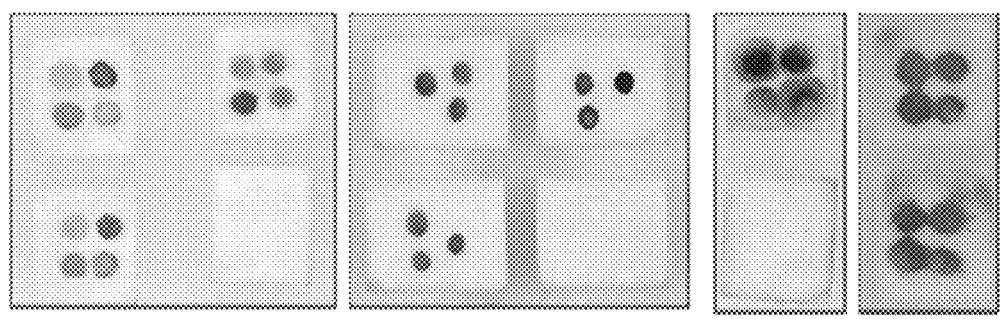
FIG. 2 are photos showing the results of a simplified flow through (FT) test using, soluble and particle-bound hydrogen donor conjugates containing biotin spotted on pure glass fiber membrane (Ahlstrom 111). Biotin was detected using an anti-biotin Ig-HRP conjugate. Upon addition of MBTH/peroxide, spotted hydrogen donor conjugates containing PQ, NED, PEDA and DMPA produced distinct spots with red, blue and violet color with a sharper image for particle-bound hydrogen donors. As a negative control for non-specific reaction, an anti-human IgG-HRP conjugate was used. No color was seen in the control membranes. Similar membranes developed with precipitating TMB substrate produced diffuse spots with significant background staining.

FIG. 2 shows examples of simplified versions of flow through tests on pure glass fiber membranes where hydrogen donor conjugates have been immobilized through passive adsorption or using particle-bound reagents. Both produce sharp colored spots on the membranes and unlike tests that used TMB substrates, there was no background staining.

Glass-fiber membranes (Fusion 5, pure glass fiber) and porous polyethylene matrix (Porex hydrophilic matrix 10-35 um pore size) work well for making diagnostic zones for flow-through tests using particles loaded with hydrogen donors.

Antigen or antibodies may be immobilized on membranes together with hydrogen donor conjugates in a free form or conjugated to carriers. For tests that use a biotin/streptavidin system to capture analyte, the test zones were prepared using hydrogen donor conjugates containing biotin. Anti-HRP antibodies may be used as an internal control zone for all tests. Anti-HRP antibodies can bind to any HRP conjugate used as a detector conjugate. Other reagents, which can capture conjugated HRP may also be used for this purpose. Anti-HRP antibodies may be simply mixed with hydrogen donor conjugates. Similar particles loaded with analyte capture reagent or anti-HRP antibodies or another reagent that bind detector HRP conjugate may also be used. For simultaneous detection of several analytes on one membrane, the test and internal control zones may be prepared with different hydrogen donor conjugates generating different colors that may be easily discriminated by the eye. The red color generated from the PQ hydrogen donor conjugates are usually associated with the internal control zone, and the violet, blue and dark blue with the test zones. Various color pallets may can be generated by mixing various reagents.

Typically, membranes for flow-through tests do not require blocking after reagents have been applied, if the assay wash buffer contains protein or detergents and a quick pre-wash step is used before the sample/detector conjugate mixture is added. Tested samples should be pre-diluted or used undiluted for mixing with HRP conjugates, which contain a reagent, which recognizes the test analyte. Sample/conjugate mixture may be applied onto diagnostic membranes directly or through a special pre-filter. After adsorption of all liquid, several washing steps may be carried out using assay wash buffer in a dropper bottle. This step should provide full removal of all unbound enzyme label. Most tests tolerate a very high concentration of HRP (up to 10 ug/ml) without effecting the specificity of the test. As a final step, 1-3 drops of substrate reagent containing coupler/peroxide (optionally with stabilizers) may be added. Color develops very quickly (within several seconds) for samples, which have a high concentration of test analyte, and require up to several minutes to attain maximum sensitivity to detect analytes at very low concentrations. Depending on the type of diagnostic membrane, the speed of filtration and the desired sensitivity, the total assay time may vary from 1 minute (for fast flow membranes, glass fiber or porous polyethylene) to 10 minutes (for nitrocellulose type membranes). In some cases, reaction times may be extended to maximize the potential of the detection system.

Fast flowing porous polyethylene material and glass fiber membranes allow for the development of very quick assays, while nitrocellulose membranes (unbacked and paper backed) usually take more time to run the tests, but in most cases, tests can be completed within 5-6 minutes.

FIG. 3 demonstrates the results from a fast, highly sensitive flow through test for the detection of antibodies and antigens on Fusion 5 and porous polyethylene membranes with assay times ranging between 2 and 5 minutes. The rapid tests have similar or even higher sensitivity than the corresponding ELISA tests utilizing the same capture and HRP-labeled reagents. The amount of coupler/peroxide substrate reagent present in the liquid phase surrounding the diagnostic zones is enough for a strong color to develop. The kinetics of dye formation with immobilized hydrogen donors is very quick, as all active/oxidized coupler produced within the zone with peroxidase is immediately consumed by hydrogen donor present in excess in the zones. This attribute significantly reduces the risk of false positive results in adjacent zones based on the diffusion of oxidized coupler from one zone to another. A distance of 2-3 mm between zones is usually enough to exclude false positive results of this type, if no excess substrate reagent is present allowing for quick diffusion of the reactive coupler between zones.

Figure 4:
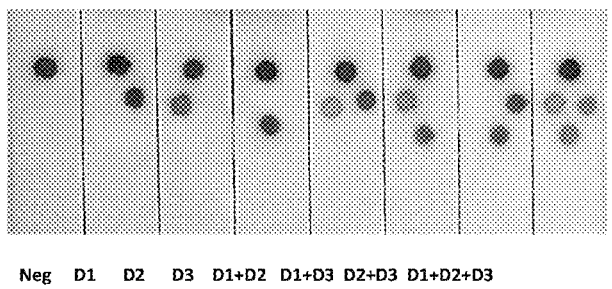
FIG. 4 is a photograph showing the results of a multiplexed lateral flow (LF) test for the detection of three analytes, one antibody D1 and two antigens (D2, D3) in a common sera sample. Test and control zones were prepared by spotting on porous polyethylene strips with particle containing mixtures of hydrogen donor conjugates and analyte capture reagents spotted a distance of 2-3 mm between each spot. A mixture of three HRP labeled reagents were used for each analyte. Samples were sera containing one test analyte or various combinations of the analytes. The analytes were detected in 5-6 minutes.

FIG. 4 shows the results of a multiplexed lateral flow test for the detection of three analytes on a porous polyethylene matrix where the test zones have various particle-bound hydrogen donor conjugates and the analyte capture reagents are spotted closely with a distance of 2-3 mm between each spot. A strong signal for each analyte does not create a false positive signal in the adjacent zones.

The absence of hydrogen donor conjugates in areas of the diagnostic membrane other than the test and control zones, completely eliminates background staining. In contrast, background staining is frequently seen in tests that use conventional precipitating HRP substrates as a result of the presence of HRP labeled reagents on membranes outside of the diagnostic zones or formation of excessive amounts of TMB precipitate products which diffuses outside of the test zones. (See FIG. 2) The absence of background staining results in a more accurate densitometric analysis.

Liquid substrate reagent containing MBTH coupler, sodium perborate as the peroxide compound in acidic (acetate-citrate-borate-EDTA buffer, (pH 5.3)) is stable and can be stored for years in a refrigerator. This substrate buffer does not dissociate antibody/antigen complexes in diagnostic zones. The stability of the liquid coupler/peroxide substrate reagent can be further improved by adding additional protective compounds for the peroxides and antioxidants, thereby preventing oxidation of the MBTH.

The reagents disclosed herein may be used to develop ultra-sensitive rapid tests utilizing lateral flow principles, immunochromatographic tests or strip tests. Lateral flow tests with an HRP label and the system described herein provides a simpler format which uses the same stable, liquid substrate reagent as the flow-through tests. This format can be described as lateral flow/dip-strip. it differs from the typical lateral flow test, which uses one liquid component, by using two liquid reagents: wash buffer and substrate. Substrate reagents may be added into specially designated zones on diagnostic strips through special windows (in the strip housing) and may quickly saturate membranes with control and test zones. As for the flow-through tests, the active couplers generated in these zones may quickly be consumed by hydrogen donor conjugates. Coupler/peroxide substrate reagents maybe prepared in stable dry form on porous materials, which may be included into diagnostic strips as special substrate pads. Dry substrate may be quickly reconstituted upon contact with an assay wash buffer to form a solution that is equivalent to a liquid reagent. Special cassettes for this type of lateral flow test are required to change the liquid flow from the wash buffer pad to the substrate pad to the diagnostic zones by lateral flow mechanisms.

As further described in the following examples, soluble and particle-immobilized hydrogen donor conjugates were used to make lateral flow tests containing multiple test zones and internal control zones for the detection of various antigens (anthrax protective antigen, human TSH, strep A polysaccharide, influenza A and B antigen) and numerous serological tests for the detection of antibodies to disease-specific peptides and recombinant antigens (Lyme test, HIV-1, SARS, cysticercosis, taeniasis, Chagas, anthrax and avian influenza). In some instances, direct comparative experiments were carried out in which the sensitivity of the lateral flow test utilizing a colloidal gold conjugate was compared with the sensitivity of a comparable hydrogen donor conjugate based tests.

EQUIVALENTS

The invention will be further described with reference to the following non-limiting examples. It will be apparent to one skilled in the art that many modifications may be made to the embodiments described below without departing from the scope of the invention. It is to be understood that these examples are provided by way of illustration only and should not be considered limiting in any way.

EXAMPLES

Materials

Polyacrylic acid of various molecular weights, polyacrylic acid co-polymers, polymaleic anhydride, and diamino-PEG (polyethylene glycol) were obtained from Polysciences, Inc (Warrington, Pa.). Various polycarboxylic polymers were obtained from Sigma-Aldrich and PolySciences, Inc. BSA (bovine serum albumin), EDAC (N-(3-dimethylaminopropyl)-N-ethylcarbodiimide hydrochloride), NHS (N-hydroxysuccinimide), HyBTz (1-hydroxybenzotriazole), DMSO (Dimethyl sulfoxide) DMFA (Dimethyl formamide), sodium borate, boric acid sodium hydroxide, hydrochloric acid, MES (2-(N-morpholino) ethane sulfonic acid), MOPS (3-(N-morpholino)propane sulfonic acid), NPC-PEG, PGA (polyglutamic acid), EDTA (ethylenediamine tetraacetic acid), EGTA (ethylene glycol-bis(2-aminoethylether)-N,N,N',N'-tetraacetic acid), MBTH (3-methyl-2-benzothiazolinone hydrazone hydrochloride), acetaminophen, sodium perborate, glycerol and the following hydrogen donors: PQ (primaquine diphosphate (8-[4-amino-1-methylbutyl]-6-methoxy quinoline), DMPA (N'N'-[Dimethyl-1,3-phenylenediamine dihydrochloride), PEDA (N-phenylethylenediamine), and NED (N-(1-naphthyl)ethylenediamine dihydrochloride) were obtained from Sigma-Aldrich. Polyethylene glycols with terminal amino groups (mono or bis), active ethers of PEG, BOC-protected PEG amine or nitrophenyl carbonate PEG, and biotin-PEG were obtained from Nektar (San Carlos, Calif.), Lysan Bio (Arab, Ala.), Sigma-Aldrich and Thermo Scientific. Polystyrene and hydrophilic polystyrene carboxylate-modified particles (CML) and amino-modified polystyrene particles were purchased from Invitrogen/Molecular Probes/Interfacial Dynamics, Bang's Lab, Polysciences and Thermo Scientific. Diagnostic nitrocellulose membranes were from Sartorius, Millipore or Whatman, glass fiber membrane with binder (Fusion 5) and GF/DNA were from Whatman (GE Healthcare). Pure glass fiber membranes were from Ahlstrom.

Porous polyethylene membranes were from Porex/Interstate specialty products (Sutton, Mass.). Stabilization solutions (StabilZyme Guard Choice, StabilZyme Select) were from SurModics. TMB (3,3',5,5'-tetramethyl-benzidine) substrates were from Moss, Inc. and KPL. Colloidal gold conjugates (StrAv-gold, protein A-gold) were purchased from EYLabs (CA), and StrAv-HRP, Protein A-HRP, biotin-HRP, anti-biotin-IgG-HRP conjugates, anti-HRP polyclonal antibodies, anti-human IgG-HRP were purchased from Sigma-Aldrich and Jackson ImmunoResearch. Dialysis membranes with various pore sizes were purchased from Spectropor. Hollow fiber dialysis cartridges were purchased from Polyscience and Bio-Rad.

Example 1

Direct Coupling of Hydrogen Donors with Primary Amino Groups to Carboxylate Modified Particles Hydrophilic carboxylate-modified latex particles (CML) with a high density of carboxylic groups and a diameter of 0.2-3.0 uM were washed with water and 0.1M MES buffer, pH 6.3 using centrifugation at 14,000 rpm for 3-5 minutes using siliconized polypropylene tubes. To a final suspension (4% solid bead volume) of washed particles, 20-40 mM solutions of donors, or mixtures of donors with biotin-PEG-amine (or diamino-PEG), in 0.1M MES, pH 6.3-6.8 were added. The concentration of biotin-PEG-amine or diamino-PEG was 10% of that of hydrogen donors, usually as a mixture, 18 mM and 2 mM, correspondingly. The final concentration of particles was 1-2% solid. Solutions of EDAC (1M in 0.1M MES, pH 6.3) and 0.4M NHS were added into tubes to a final concentration of EDAC and NHS in reaction mixtures, 0.1M and 0.04M, respectively. Reactions proceeded with gentle shaking for 60-90 minutes at room temperature. Particles were purified by several cycles of centrifugation with subsequent vortexing, using wash buffer of 0.3M NaCl, 50 mM sodium phosphate, 1 mM EDTA, pH 7.6 with detergent Triton X-100 (0.1%) or fluorinated detergent PolyFox NP154, and finally in PBS (phosphate buffer solution) with 1 mM EDTA or StabilGuard Choice with 0.05% detergent (immunoassay stabilizer for particles). Particles loaded with hydrogen donors by this procedure and maintained with StabilGuard Choice stabilizer produced stable suspensions without visible agglutination. Particles could be stored for at least several months (or up to year or longer) without reducing the activity or accumulating colored oxidation products. Particles loaded with hydrogen donors are white for NED and PEDA donors, have very light yellow/brown residual pigmentation for PQ donors and sometimes very light violet pigmentation for DMPA donors. Upon impregnation into white membranes at amounts that generate strong colored dyes in reactions with an oxidizable coupling reagent, these particles produced zones that are almost invisible on the white background.

Example 2

Coupling of Hydrogen Donors with Carboxylate Particles Through BSA/Polyacrylic Acid or BSA/Polymaleic Acid Spacers Washed hydrophilic carboxylate particles prepared as described in Example 1 were first activated with EDAC/NHS in suspension (1-2% solid particle volume) in 0.1M MES, pH 6.3 with 0.1 M EDAC and 0.04 M NHS for 30 min. Activated particles were centrifuged and resuspended in 0.1M MES, pH 6.8 to a concentration of 1% solid. BSA solution in 0.1M MES, pH 6.8 was added to final BSA concentration 5 mg/ml. Coupling reaction proceeded for 60 min with gentle shaking Particles with immobilized BSA were washed several times with PBS-EDTA and finally with 0.1M MES, pH 6.3. BSA particles could be used for direct loading with hydrogen donors or additionally modified with polyacrylic acid or polymaleic anhydride to increase the density of carboxyl groups.

For loading onto BSA particles, polyacrylic acid (MW 2K, 6K or 15K) was first activated at a concentration of 5% with EDAC/NHS (0.1M/0.04M) in 0.1M MES, pH 6.3. Activation proceeded for 30 min, followed by conjugation to BSA particles. For conjugation, activated polyacrylic acid was added at 5 mg/ml to a 1% BSA particle suspension and incubated for 60 min with gentle shaking.

BSA-polyacrylic acid particles were purified by two centrifugations using 0.1M MES, pH 6.8 as wash buffer and finally resuspended to 2% (v/v) in the same buffer. Solutions of donors or donors-biotin-PEG were then added to make mixtures containing 1% particles and ~10 mM donor or donor-biotin-PEG. EDAC and NHS were added to final concentrations of 0.1 M and 0.04M, respectively. Reaction proceeded for 60 minutes with shaking Particles loaded with donors were purified as described in Example 1.

For reaction of BSA particles with polymaleic anhydride, particles were washed twice in 0.1M borate buffer, pH 8.8 and resuspended to a concentration of ~2% solid. Solution of 50 mg/ml polymaleic anhydride (MW 5,000, PolySciences) in DMSO was added at a ratio of 25 ul per 1 ml of BSA particles and incubated for 60 min at room temperature while shaking BSA-polymaleic acid particles were purified by centrifugation, twice with PBS and twice with 0.1M MES, pH 6.3.

Conjugation of BSA-polymaleic acid particles with hydrogen donors and purification was accomplished as described above for BSA or BSA-polyacrylic acid particles. Particles modified with hydrogen donors through BSA, BSA-polyacrylic acid and BSA-polymaleic acid produced exceptionally stable suspensions without aggregation. Particles loaded with hydrogen donors using BSA-polycarboxylic polymers have a higher density of hydrogen donor as evidenced by their activity in colorimetric tubes and membrane tests as described in the examples below.

Example 3

Synthesis of Water Soluble Polycarboxylic Polymer-Hydrogen Donor Conjugates 3.1. BSA-EDTA/EGTA-Hydrogen Donors/PEG-Biotin Conjugates.

Hydrogen donors can be coupled with BSA directly using the EDAC/NHS activation chemistry described for the synthesis of particle-based donors. However, higher loading of hydrogen donors to BSA can be achieved by modifying the amino groups of BSA with a low molecular weight, branched tetra-acetic molecule such as EDTA and EGTA, as described below.

EDTA and EGTA at 0.25M were partially activated with 50 mM EDAC/20 mM NHS in 0.1M MES, pH 6.3. At these concentrations, ~25% of the available carboxyl groups in tetracetic acid compounds are activated. The activation reaction proceeded for 30 minutes and activated EDTA or EGTA were added immediately into 80-100 mg/ml BSA solution in 0.1M MES, pH 6.3 to make reaction mixtures containing BSA at 40-50 mg/ml and a concentration of activated tetraacetate compound at 125 mM. Reaction mixtures were incubated for 60 minutes and purified by dialysis against PBS- EDTA and finally against 0.1M MES, pH 6.3 using a dialysis membrane with a cut-off of 12-14 kDa.

For coupling of hydrogen donors to EDTA-BSA or EGTA-BSA, solutions of modified BSA and hydrogen donors/amine-PEG-biotin in 0.1M MES, pH 6.3 were mixed to produce solutions containing 15-20 mg/ml modified BSA and 12 mM hydrogen donor/amine-PEG-biotin. EDAC and then NHS were added to final concentrations of 50 mM and 20 mM, respectively. After incubation for 60 minutes, the conjugates were dialyzed against PBS-EDTA using a dialysis membrane with cutoff of 12-14 kDa.

3.2. BSA-PEG-Polycarboxyl Polymer-Hydrogen Donors-PEG-Biotin Conjugates.

Preparation of soluble hydrogen donor conjugates in this example included three major steps: a) hydrophilization of BSA with PEG through a partial modification of the available amino groups, b) conjugation of PEGylated BSA with polycarboxylic polymers, and c) conjugation of BSA-PEG-polycarboxylic polymer with hydrogen donors/amine-PEG.

Several reagents were used for PEGylation of BSA with partial modification of available amino groups in the protein, such as PEG-nitrophenyl carbonate, MW 5,000 (NPC-PEG), PEG-succinimidyl succinate (MW 10000), as well as BOC derivatives (NPC-PEG-BOC, amine-PEG-BOC, SS-PEG-BOC).

For partial modification of amino groups in BSA with NPC-PEG, dry NPC-PEG was added into 80-100 mg/ml BSA solution in 0.1M borate buffer, pH 8.1, at the molar ratio of 6 PEG per BSA (0.5 mg NPC PEG MW 5000 per 1 mg BSA) and reacted at room temperature for 3 hours. The reaction mixture was dialyzed extensively against 2×PBS, 1×PBS and finally against 0.1M MES, pH 6.3, using a 25 kDa dialysis membrane. Alternatively, purification was performed by hollow fiber (50K pore size) dialysis.

For partial modification of available amino groups of BSA with succinimidyl PEG, DMSO solution of these reagents (10 mg/ml) were added into BSA solution (50-60 mg/ml) in 0.1M MOPS buffer, pH 7.6, at a molar ratio of PEG/BSA of 6:1 and reacted for 1-1.5 hours with subsequent dialysis as described above for NPC-PEG-BSA. Reaction products were analyzed for the presence of amino groups using a TNBS (trinitrobenzene sulfonic acid) test and by size-exclusion HPLC.

Polyacrylic acids (MW 1,800, 2,000, 3,500, 6,000 or 15,000) were activated with EDAC/NHS in a solution with 10% (w/v) polymer in 0.2M MES, pH 6.3. The amount of EDAC (2M in water) and NHS (0.8M in water) added was equivalent to activation of ~10% of the available carboxyl groups in a polyacrylic acid solution. The reaction proceeded for 30 minutes, after which activated polyacrylic acid was added to BSA-PEG solution in 0.1M MES, pH 6.3. A typical ratio of BSA-PEG:polyacrylic acid was approximately 1:5 in a reaction mixture containing 15-25 mg/ml BSA-PEG. Reaction time was 60 minutes at room temperature. BSA-PEG-polyacrylic acid conjugates were purified by extensive dialysis against PBS-EDTA and finally against 0.1M MES, pH 6.3 using a 25K dialysis membrane.

For modification of residual amino groups in BSA-PEG with poly-maleic anhydride, thus introducing extra carboxyl groups, PEGylated BSA was dialyzed against 0.1M borate, pH 8.8. Maleic anhydride (MW 5,000) was added from 100 mg/ml solution in DMSO into BSA-PEG solution (20-40 mg/ml) as a single aliquot to produce a ratio of BSA:polymaleic anhydride of 1:20, or as three aliquots with immediate adjustment of pH to ~8.2 with 1N NaOH. Mixtures with added polymaleic anhydride were incubated for 30-60 minutes and then extensively dialyzed against 2×PBS, 1×PBS and finally against 0.1M MES, pH 6.3 using a 25K dialysis membrane.

For coupling of BSA-PEG-polycarboxylic acid with hydrogen donors/amine-PEG-biotin or donors/amine-PEG-amine solutions at a concentration of 18 mM/2 mM (hydrogen donor/PEG) in 0.1M MES, pH 6.3 were mixed with BSA-PEG-polycarboxylic acid conjugate in the same buffer at a ratio of 2 volumes donor/PEG per 1 volume BSA-PEG-polycarboxylic acid at a concentration of BSA in a range of 15-25 mg/ml. EDAC (2M in water) and NHS (0.8M in water) were added to final concentrations of 0.1M and 0.04 M, respectively. After 60-90 minutes incubation, reaction mixtures were extensively dialyzed against PBS-EDTA using a 25K dialysis membrane.

For further lyophilization, conjugates were dialyzed against 1 mM EDTA, pH 7.6 using a 25K dialysis membrane and freeze-dried in glass vials. Most conjugates reconstitute quickly and completely in PBS-EDTA or water producing clear solutions with a small residual brownish color for PQ conjugates.

3.3. Polyacrylic Acid-Hydrogen Donors-PEG Conjugates.

Preparation of these types of soluble hydrogen donor conjugates involved one major step, the incubation of mixtures of polyacrylic acid, hydrogen donors and PEG-amine (or biotin-PEG-amine) with the activation reagents, EDAC and NHS.

In a typical protocol, mixtures were prepared containing 20 mg/ml polyacrylic acid (MW 15K, 225K, 345K), 30 mM hydrogen donors, 3 mM PEG-amine (MW 3.5K, 5K or 10K), 2 mM biotin-PEG-amine (MW 2K, 3.5K or 5K) in 0.1M MES, pH 6.3-6.7 2M EDAC and 0.8M NHS solution in water were added to final concentrations of 0.2M and 0.08M, respectively. Mixtures were incubated for 60-90 minutes. Conjugates were purified by dialysis (25K membrane) against 2×PBS-EDTA and 1×PBS-EDTA. All conjugates were clear solutions with small brown pigmentation for PQ conjugates.

All conjugates produced invisible zones when applied on membranes at concentrations within the binding capacity of the membrane. All soluble hydrogen donor conjugates described above can be stored in a liquid form at least several months, in a frozen form or freeze-dried after dialysis against water or 1 mM EDTA, pH 7.0.

Freeze-dried preparations based on high molecular weight polyacrylic acid can be quickly and completely reconstituted with water or buffers to form clear solutions. Dried low molecular weight polyacrylic acid conjugates dissolve in water more slowly.

Example 4

Passive Adsorption of BSA-PEG-Hydrogen Donor Conjugates on Polystyrene Particles Polystyrene particles (0.8-0.95 uM) were washed with PBS-EDTA by repeated centrifugation at 14,000 rpm for 6 minutes and finally resuspended in this buffer at 5% bead volume. Particles were loaded with BSA-PEG-donor at a ratio of 0.1-0.15 mg BSA per mg solid particles.

For adsorption of BSA-PEG-donor, solution in PBS-EDTA was added to particles prepared in the same buffer. Mixtures containing approximately 1% particle volume were incubated by shaking for 1 hour and then left stationary overnight at 4° C. Particles were purified by two centrifugation washings with PBS-EDTA (with vortexing) and finally resuspended at 2% particle volume.

Example 5

Covalent Coupling of BSA-PEG-Hydrogen Donor Conjugates with Carboxylate-Modified Particles 5.1 Coupling with Carboxylate Particles.

Hydrophilic carboxylate-modified polystyrene latex particles (CML particles, 0.78-0.9 um size range, Interfacial Dynamics) were washed with 0.1 mM MES, pH 6.5 and resuspended in this buffer. BSA-PEG-hydrogen donor conjugates with available amino groups, synthesized by coupling hydrogen donors/amine-PEG-amine to BSA-PEG-polycarboxylic conjugates, were dialyzed against 0.1M MOPS, pH 7.8. Washed particles in 0.1M MES, pH 6.5 were activated in 2% suspension with EDAC/NHS (0.1M/0.04M) for 25 min. Activated particles were quickly washed once by centrifugation and resuspended in 0.1M MOPS, pH 7.8 to 2% solid. BSA-PEG-hydrogen donors-PEG-amine conjugates were added to particle producing mixtures containing 1% particle solid and BSA conjugate at concentration approximately 1 mg/ml. Mixtures were incubated for 60 minutes with mild shaking and then overnight in a refrigerator, after which they were purified by three centrifugations using PBS-EDTA as a wash buffer. Particles were finally resuspended at 2% solid in PBS-EDTA or additionally blocked with StabilGuard Choice for storage. Both carboxyl latex and hydrophilic CMC latex particles produced white stable aggregate-free suspensions, which were easily resuspended from pellets.

5.2 Coupling with Aminated Particles.

Carboxylate-modified latex particles as described above were converted into amino-modified particles by reacting 1% solid suspension CML particles with 0.25M ethylenediamine, 0.1/0.04M EDAC/NHS, pH 6.3 for 90 minutes. Ethylendiamine-modified particles were washed 5 times with 0.1M MES, pH 6.5. BSA-PEG-polycarboxylic polymer-donor conjugates were synthesized as described in example 3.2 at a ratio of amine-hydrogen donor/PEG-amine to carboxyl groups of BSA-PEG-polycarboxyl polymer allowing partial, 30-50%, modification of available carboxyl groups on the BSA-PEG-polycarboxylic acid polymer. For coupling of amino groups on ethylendiamine-modified particles with BSA-PEG-hydrogen donor conjugates, particles were mixed with BSA-PEG-polycarboxylic polymer-donor conjugates at a ratio of 0.1-0.2 mg BSA per mg particle solid in a suspension at 1% solid. EDAC and NHS were added to mixture amine-particles/BSA-PEG-polycarboxylic acid polymer-donor conjugates to a final concentration of 0.05 and 0.002 M. The reaction time was 90 minutes at shaking Particles were washed with PBS, and PBS-EDTA.

Example 6

Synthesis of Analyte Capture Reagents and Other Supplementary Reagents

Additional particle-based reagents were synthesized using the same carboxylate particles as described in previous examples. Among these particles were: biotinylated particles, particles with covalently immobilized anti-HRP antibodies, streptavidin, glucose oxidase, peptide and protein antigens and antibodies against various bacterial and viral antigens, and hemoglobin. Various methods for immobilization were used, including: activation of carboxyl particles with EDAC/NHS, using cross-linking reagents (maleimide/sulfhydril) for cross-linking with BSA modified carboxylic particles, or aminated particles or activation of aminated particles with glutaraldehyde. HRP was conjugated with antibodies using the periodate method with reduction of the Schiff base with sodium cyanoborohydride or using sulfhydryl reactive cross-linking reagents.

Example 7

Oxidizable Coupling Reagents 7.1.

MBTH-peroxide solution substrate reagent was prepared in acetate-borate-citrate buffer containing 0.1 M sodium acetate, 10 mM boric acid, 10 mM citric acid, 1 mM EDTA, adjusted to pH 5.3 with sodium hydroxide. MBTH hydrochloride was added from 40 mM stock solution in water to a final concentration of 1, 2 or 4 mM; sodium perborate was added to concentrations of 4 or 8 mM. Additionally, stabilized liquid substrates were prepared by adding 1 mM acetaminophen to substrates described above. This substrate can be used for up to two years if stored in a refrigerator.

In an accelerated stability study, the substrate demonstrated no change in activity during a 28-day storage at room temperature and only a 10% decrease in activity after storage for 28 days at 37° C.

7.2.

MBTH-perborate substrate reagent was prepared in 0.1M MES, 0.1M sodium borate, 1 mM EDTA, pH 5.3. MBTH and sodium perborate were added into this buffer to a concentration of 2 mM and 8 mM, respectively.

0.8-ml aliquots of this substrate were lyophilized in glass vials overnight. Dry substrate is a white, not hydroscopic, fluffy solid, which is easily dissolved in water. A comparison of the activity of reconstituted freeze-dried substrate with control substrate stored as a liquid as described in Example 8 below, detected no difference in activity.

Example 8

Analysis of the Activity of Soluble Hydrogen Donor Conjugates in Solution

The activity of hydrogen donor conjugates in reactions with oxidative coupling reagents was tested in microplates. BSA-hydrogen donor conjugates and hydrogen donor-polyacetic acid were replaced for generic hydrogen donor conjugates which cover both hydrogen donor conjugates with BSA-polycarboxylic polymer by adding 10-20 µg hydrogen donor conjugates as BSA or polyacetic acid polymer into wells with MBTH-perborate substrate, pH 5.3, with 1 mM MBTH and 4 mM sodium perborate. The oxidation reaction was initiated by adding 5 µl of 1 µg/ml HRP solution in BSA-based immunoassay stabilizer (StabilZyme Select, SurModics). Dye formation was monitored by reading the absorbance spectrum of the reaction products in a spectromax 250 spectrophotometer (Molecular Devices) in the range of 450-650 nm.

Absorbance max for dyes produced with soluble PQ conjugates lie in the range of 500-520 nm depending on the intensity of color, which is visually bright red. DMPA conjugates produced dyes with absorbance max in the range of 540-550 nm, which is visually a gradation of violet/pink color. NED conjugates generated dyes with absorbance maximum in the range of 570-590 nm, which is a dark blue color. PEDA conjugates produce dyes with absorbance max of 550-570 nm, appearing as light violet color.

When reacted with MBTH, most conjugates produced dyes which are also soluble and remained in solution even at high concentrations of reaction products. In the absence of enzyme, most mixtures of hydrogen donor conjugates with MBTH and peroxide have no visible traces of spontaneous oxidation and dye formation during long incubation times even without being protected from light.

Example 9

Testing the Activity of Particle-Immobilized Hydrogen Donors in Solution 20-30 µl particles (0.4-2.0 um) containing hydrogen donors were mixed with 500 µl MBTH-peroxide substrate in 1.5 ml clear Eppendorf tubes and 5 µl of 1-2 µg/ml streptavidin-horse radish peroxidase (StrAv-HRP) solution was added. The mixtures were incubated for 15 minutes while shaking and centrifuged for 2-3 minutes at 14,000 rpm. The particle pellet contained intensely dyed particles and the supernatant for most particle conjugates was almost clear, indicating the absence of non-bound fractions of hydrogen donors. Particles containing PQ hydrogen donor had a bright red color. DMPA particles had a bright violet color. NED particles had bright dark blue color. PEDA particles had a light violet color. The color of dyed particles in sediment did not change during long storage at room temperature, even without being protected from light.

Example 10

Testing the Activity of Particle-Immobilized Hydrogen Donors on Membranes and Other Porous Materials 10.1

Particles with immobilized hydrogen donors and their mixtures with other particles (e.g. with anti-HRP antibodies, biotin, streptavidin. or glucose oxidase) were applied on Fusion 5 membranes using the reagent dispenser Linomate 5 (CAMAG). Membranes were laminated onto a backing card with an adhesive. The concentration of particles with immobilized hydrogen donors was 0.5-2% solid in StabilGuard Choice with 0.05-0.1% PolyFox NP-154 in PBS-EDTA or in buffer containing 4% sucrose and 2% PEG-4000 as stabilizers for application of particles containing immobilized antibodies. The dispensing volume was 0.5-2.0 µl/cm. Supplementary particles, if necessary, were added in to the striping mixture in an amount of 5-20% of hydrogen donor particles. Membranes were dried at 45° C. for 15 minutes in an oven (food dehydrator) and cellulosic adsorbent pad material was attached to one end of Fusion 5 membranes. Strips 4-6 mm wide were prepared using a guillotine membrane cutter (index cutter, Kinematic Automation).

10.2.

Particles with hydrogen donors were applied on strips, discs or squares of glass fiber membranes (Fusion 5, Ahlstrom grade 111) and on porous polyethylene (Porex type 4897, 15-45 um pore size, 0.062"), as spots with volumes of 1.0-3.0 µl/spot (depending on the material), using the buffer solution described above and dried at 45° C. for 15 minutes. The porous polyethylene membrane strongly retained particles of various sizes (0.4-3.0 uM) despite its large pore size.

10.3.

Soluble hydrogen donor conjugates and their mixtures with other components of analyte capture systems were applied on nitrocellulose membranes using solutions in PBS-EDTA, or additionally containing 4% sucrose. Solutions were applied using the reagent dispenser Linomate 5 at a dispensing volume of 0.5-1.0 µl/cm. The concentration of hydrogen donor conjugates was in the range of 0.25-1.5 mg/ml for most tests. After drying at 45° C. for 10-15 minutes, sample/wash buffer pad (Fusion 5) was attached from one end and adsorbent pad material from the opposite end of the backing card with approximately 1 mm of overlap. Strips 4-5 mm wide were prepared using a guillotine cutter.

For testing of reagents in a flow-through format with a nitrocellulose type membrane, spots of soluble hydrogen donors/capture reagents (0.3-0.6 µl) were applied on squares of nitrocellulose membrane with paper backing (FT 060, Whatman) and dried.

10.4.

For testing of reagents in a flow-through format with a pure glass fiber membrane, Ahlstrom 111 particles with hydrogen donors or soluble BSA-polyacrlylic acid conjugates in PBS-EDTA were spotted (1-2 µl/spot) and dried as described above. Test samples for most analytical tests were prepared in sample diluents containing 10% calf sera in the immunoassay stabilizer StabilZyme Select, detergent 0.1% Triton X-100 or Tween-20 and dye orange G at a concentration of 0.005%. Wash buffer contained BSA at 5 mg/ml, 4% glycerol, 0.1% Triton X-100 and 1 mM EDTA in PBS, pH 7.2.

10.5. Typical Assay Protocols for Testing Hydrogen Donor Conjugates Applied on Fusion 5 Glass Fiber Membranes.

Sample containing HRP conjugate recognizing capture reagent, co-immobilized with hydrogen donor particles (anti-Biotin IgG-HRP, StrAv-HRP, Protein A/G-HRP, biotin-HRP, anti IgG-HRP) in lines was applied on strips in the area between lines with donors/capture reagents and wash buffer application zone. The sample volume was 20-40 µl. Wash buffer was added dropwise directly on the end of Fusion 5 or on a square of Porex porous polyethylene membrane placed on the end of a Fusion 5 strip. An additional piece of adsorbent pad was placed over the adsorbent pad attached to strips.

Washing continued for 1-1.5 minutes until complete wash out (disappearance of orange color) of Orange G dye. Substrate solution, one 30-40 µl drop, was added into the same zone as sample or directly on lines with hydrogen donors. A strong signal became visible several seconds after contact with substrate, and a weak signal required several minutes for color development. The total assay time was in the range of 1.5-6 minutes. To analyze the kinetics of dye formation, sequential pictures were taken using a photo camera. To stop the reaction and dye formation, extra wash buffer or special stop solution containing 50 mM hydroxylamine and 0.5% SDS in wash buffer was added on a wash buffer pad.

For testing hydrogen donor conjugates spotted on strips of porous polyethylene, 10-mm wide strips were laminated onto an adhesive backing card. 50-100 µl sample was added into area behind spots. No special wash buffer pad was used. An adsorbent piece of cellulosic membrane was placed on one end of the strip. After sample application, wash buffer was added using a dropper bottle until all orange G dye entered into the adsorbent pad. Several drops of substrate were added directly on zones with spotted reagents. Dye formation took seconds or extended for several minutes depending on the amount of captured HRP label. Total assay time was 1.5-8 minutes.

For testing reagents in flow-through (vertical filtration format), squares or disks of membranes with spotted reagents were inserted into appropriate flow-through cassettes with thick adsorbent material below membranes, providing direct contact between diagnostic membrane and adsorbent or through an additional layer of porous polyethylene membrane (Porex type 4588, 90-120 um, 0.024"). Before sample application, membranes were wetted with 2-3 drops of wash buffer, and 100-200 µl of sample containing HRP-labeled detection reagents was added. After complete absorption of liquid sample, 4-5 aliquots of wash buffer was added using dropper bottles allowing for the complete absorption of the deposited solution. Then 3-4 drops of substrate were added. Dye formation in spots took place within seconds for highly positive signals, with read time extending up to 5 minutes for less positive signals. At the end of incubation with substrate, membranes were quickly washed and removed from cassettes for analysis (to prevent false positive signals as a result of back diffusion of the enzyme).

Example 11

Analytical Sensitivity of Hydrogen Donor Conjugates Vs. Colloidal Gold Label in a Lateral Flow Test Format 5-mm strips of Fusion 5 membrane with a test line containing 1.2 µm CML particles with immobilized DMPA hydrogen donor and biotin-PEG prepared as described in Examples 1 and 10.2 were tested with serially diluted conjugates containing StrAv-gold, StrAv-HRP, anti-biotin IgG-gold or anti-biotin IgG-HRP. Liquid samples (30 µl) containing StrAv or anti-biotin antibodies in amounts ranging from 120-0.0075 ng per sample were applied in simultaneous experiments on two sets of strips—one for gold conjugate and the other for HRP. The testing protocol was as described in Example 10.5.
Test Results:
The smallest amount of StrAv in StrAv-Gold conjugates which produced visible lines was around 7.5 ng/strip, whereas StrAv-HRP could be easily detected at an amount of 0.0075 ng/ml, (i.e. 1000 times less). For anti-biotin IgG-gold conjugates, the minimal amount of IgG for a barely visible signal was 3.75 ng/strip, while for HRP conjugate the lines were visible with at least 0.003 ng/strip, i.e. at ~1000-fold lower amount.

Example 12

Comparison of the Analytical Sensitivity Between Colloidal Gold and Instant Disclosed Detection System in a Lateral Flow Format 5-mm strips of Fusion 5 membrane with a line containing 2 µm CML particles with immobilized PQ and biotin-PEG were prepared as described in Examples 1 and 10.2. Samples containing serially diluted StrAv-human IgG conjugate with a known concentration of conjugated IgG in a range of 24-0.012 ng/strip were applied to the strips. The amount of StrAv-IgG was significantly lower than the binding capacity of biotin in the test line. After washing, liquid protein-A-gold conjugate (30 µl, containing 6 µg/ml protein A/ml) was added on the first set of strips and 30 µl HRP-protein A at a concentration of 1 µg/ml was added on a second set of strips. Strips were washed, and strips with protein A-HRP were developed with substrate (5 minutes).
Test Results:
Protein A-gold conjugates detected IgG in amounts as low as 6 ng/strip, whereas protein A-HRP detected IgG in amounts as low as 0.012 ng/strip (i.e. 500 times lower.) The red color generated for positive signals with PQ donors is visibly brighter than the red color of bound gold conjugate.

Example 13

Comparison of the Analytical Sensitivity Between the Instant Disclosed Detection System and a System Based on Precipitation of TMB Substrate 5-mm strips of Fusion 5 membrane with a test line containing 0.8 um CML particles with immobilized DMPA or NED hydrogen donors and biotin-PEG were prepared as described in Examples 1 and 10.2. 30 µl liquid samples containing StrAv-HRP with 3-0.0075 ng HRP per sample were applied on strips. The same samples were analyzed in an ELISA test using plates coated with Biotin-PEG-BSA and ultrasensitive TMB substrate (Moss, Inc.). In ELISA experiments, the sample volume and volume of TMB substrate were 100 µl/well. Incubation times were 15 minutes with StrAv-HRP and 4 minutes with TMB substrate, with shaking. The reaction was stopped with 100 µl/well of universal stop solution.
Test Results:
HRP in StrAv-HRP conjugate can be detected at amounts of less than 0.75 pg/strip (25 pg/ml). Titrations of the same serially diluted samples of StrAv-HRP conjugates on plates coated with biotin-PEG-BSA, detected HRP at concentrations as low as 60 pg/ml. In other words, the membrane test with hydrogen donor conjugates were more sensitive than the microplate ELISA with the highly sensitive TMB substrate.

Example 14

Comparison of the Analytical Sensitivity of: (a) a Commercial Lateral Flow Test, which Uses Colloidal Gold Labels; (b) a Lateral Flow/Dip-Stick Test, which Uses HRP Labels and Immobilized Hydrogen Donors and (c) a Plate ELISA Test To compare the sensitivity of a lateral flow/dip-strip test as described herein and a commercial lateral flow test based on the conventional colloidal gold label (BINAX NOW Strep A test), polyclonal antibodies that were used in the commercial test were conjugated with HRP using a periodate procedure and covalently immobilized on 2 µm carboxylate particles. As internal positive control, polyclonal anti-HRP antibodies were conjugated with 2 µm amine particles using bi-functional cross-linking reagents (GMBS (4-Maleimidobutyric acid N-hydroxysuccinimide ester) and SATA (N-Succinimidyl-5-acetylthioacetate)). For making the test line, particles with anti-Strep A IgG were mixed with carboxylate particles containing immobilized DMPA/PEG in a ratio of 1:4. For the internal positive control line, particles with immobilized anti-HRP IgG were mixed with CML particles containing immobilized PQ/PEG in a ratio of 1:6. Mixtures were striped on Fusion 5 membranes laminated on adhesive backing and dried at 45° C. for 15 minutes. The areas containing test and internal positive control lines were laminated with 14 mm clear film. 5 mm wide strips were cut. As an adsorbent pad, thick cellulosic blotting paper (VWR 320) was attached to Fusion 5 strips. Samples for testing were prepared by mixing 10 µl HRP conjugate (2 µg/ml) and 40 µl antigen solution in sample diluent. The whole mixture was added directly on Fusion 5 membranes, 10-15 mm below the test line, but was not covered with clear film. Using a dropping bottle, 3 drops of wash buffer were added onto the wash buffer application area of the membrane and 3 more drops were added over 4 minutes (total 6 drops). After complete absorption of the wash buffer, 2 drops of substrate solution were added onto the Fusion 5 membrane in the zone where sample/conjugate mixture was applied. After 1 minute, adsorbent pad was removed and reaction with the substrate proceeded for 4-6 minutes. To stop the substrate reaction, a new adsorbent pad was placed on the Fusion 5 membrane and washing continued using ICT Wash buffer or stop solution containing SDS and hydroxylamine. The result was read by visual evaluation and pictures were taken soon thereafter.

As a control for the efficacy of the capture system for Strep A antigen on Fusion 5 membrane, a special analysis was done with detection of Strep A antigen using colloidal gold conjugates similar to gold conjugates used in the commercial test. In this experiment, 30 µl aliquots of anti-Strep A IgG-gold conjugate (5 OD units/ml) was dried on a Fusion 5 membrane about 15 mm from the test line. At testing, sample was applied on Fusion 5 membrane just in front of the dry gold conjugate. Wash buffer was added to provide a complete migration of colloidal gold conjugate through test and control lines. The control line in this experiment contained 1.0 µm particles with covalently immobilized anti-rabbit IgG.

For testing the commercial lateral flow test, 100 µl of sample was added onto the sample application/extraction window on one leaf of a book-type device. After 1 minute, adhesive liner was pealed out and the book closed. The result was read after 5 minutes.

Plate ELISA Test.

High binding polystyrene plates (Costar) were coated with rabbit anti-Strep A IgG at 4 µg/ml, and blocked with StabilZyme Select. Samples were serially titrated into wells (100 u/well) using sample diluents containing 10% calf sera in StabilZyme Select and 0.1% Tween-20. Incubation time with sample was 30 minutes while on a plate shaker. After washing with PBS-0.05% Tween-20, anti-Strep A-IgG-HRP was added at a concentration of 0.25 µg/ml. The incubation time with the HRP conjugate was 15 minutes with shaking. The plate was washed four times and developed with ultrasensitive TMB one-component substrate (Moss, Inc.) for 4 minutes at shaking. The reaction was stopped with 100 µl universal stop solution and the result was read at 450 nm.

Three types of samples with Strep A antigen were used for the analysis: a) suspension of cell culture with a known density of cells and whole cells dried on swabs (positive control swabs), b) extracted Strep A cells (nitrous acid and enzymatic), and c) pure Strep A polysaccharide conjugated with BSA at known BSA/polysaccharide ratios. As negative controls, identical aliquots of sample diluents (or sample diluents with extraction reagents used for sample preparation) were run in all tests.

Results:

A comparison of the detection limits after testing the various antigenic materials in the three test formats is shown in Table 1. The lateral flow/dip-strip test with the new substrate system for HRP had the lowest detection limit. The rapid test described herein has a detection limit of up to five times lower than the detection limit of the ELISA test and 60-600 times lower than the detection limit of the colloidal gold ICT test. Fast flow Fusion 5 strips used for the new ICT test worked with colloidal gold conjugates demonstrating a sensitivity of only 2 times lower than commercial test on a slow nitrocellulose membrane.

The rapid tests disclosed herein have the ability to detect 20 Strep A cells per test or $4.5 \times 10^2$ cells/ml in the original sample. The detection limit for BSA-PSA conjugate is 0.8 ng/ml or 0.04 ng/strip, corresponding to a concentration of polysaccharide of 0.013 ng/ml or 0.65 pg/strip. This amount is equivalent to the dilution of the original BSA-PSA stock solution (with BSA concentration 1 mg/ml) 1,024,000 times. At testing of very high doses of antigen (10 µg/ml, 2 µg/ml and 1 µg/ml), indicated no visible hook effect. Strong signal developed as a sharp bright color line within seconds after adding the substrate. Negative controls did not develop color after at least 15 minutes contact time with the substrate and remain negative for a long time if a stop reagent is applied.

TABLE 1

Comparison of the detection limit for Strep A antigens at testing in NOW Strep A ICT, new ICT and ELISA.

| | Commercial Strep A ICT - colloidal gold | New ICT/dip-strip test with immobilized hydrogen donors | ICT/dip-strip test with Gold conjugate on strips containing immobilized hydrogen donors | ELISA test with reagents used ICT tests | Ratio Detection limit ELISA/new ICT | Ratio detection limit Commercial Strep A ICT/new ICT |
|---|---|---|---|---|---|---|
| Assay time | 5-15 min | 5-12 min | 10-15 min | 60 min | | |
| Limit of detection pure antigen (BSA-PSA conjugate) | 250 ng/ml or 25 ng/strip | 0.8 ng/ml or 0.04 ng/strip* | 500 ng/ml BSA-PS A/ml or 50 ng/strip | 1.5-3 ng/ml | 2-5 | 300-600 |
| Limit of detection Strep A cells extracted with Lys enzyme | $8 \times 10^4$ cells/ml or $8 \times 10^3$ cells/strip | $4.2 \times 10^2$ cells/ml or ~20 cells/strip | n/a | $5\text{-}8 \times 10^3$ | 2-5 | 180-400 |
| Limit of detection Strep A positive swabs after standard nitric acid extraction | Dilution 1:16 | Dilution 1:1024 | n/a | n/a | n/a | 60-120 |

*As BSA content

Example 15

Rapid Tests for Detection of Anthrax Protective Antigen (PA) and Human Thyroid Stimulating Hormone (hTSH)

Rapid tests for detection of two antigens, anthrax PA and hTSH, were prepared using Fusion 5 as the diagnostic membrane and particle-based reagents as the capture reagents for the test and control lines. Capture monoclonal antibody against the beta subunit of hTSH was immobilized on 0.8 µm amine polystyrol latex particles activated with glutaraldehyde or on 0.9 µm carboxyl particles conjugated with BSA and activated with GMBS. Thiolated antibody prepared with limited SATA modification was coupled to BSA-maleimide particles. Monoclonal anti-bacillus anthracic PA antibody was immobilized on 0.8 µm carboxyl particles activated with EDAC/NHS as in Example 2. As detector conjugates for the anthrax PA test, affinity purified goat IgG-HRP or recombinant ScA fragments of antibodies conjugated with HRP were used. As a detector reagent for the hTSH test, a monoclonal anti-alpha subunit of hTSH and polyclonal affinity purified anti-beta subunit antibodies conjugated with HRP were used.

Particles with capture antibodies were mixed with particles containing immobilized hydrogen donors for making test lines on diagnostic membranes (60% donor particles, 40% particles with capture antibodies in 2% suspension). For the PA test, 0.6 µm CML particles were loaded with BSA-polyacrylic acid 15K and NED/PEG. For the hTSH test, similar NED or DMPA hydrogen donor particles were made using 0.4 µm CML particles. Reagents were striped on Fusion 5 membranes laminated on adhesive backing cards as described in Example 14. 5-mm strips were assembled with cellulosic adsorbent pad.

hTSH standard 1000 Units/ml and recombinant PA (63 kDa fragment, List Biological Laboratories) were used as antigens. Antigen dilutions for testing were made using sample diluents containing StabilZyme Select with 10% calf sera, 0.1% Tween-20 and Orange G as a dye. Samples of 50 µl were mixed with 20 µl HRP conjugate prepared in the same diluents and after short incubation (15-30 seconds), 30 µl were transferred onto strips close to the test line. The concentration of HRP conjugate in mixtures with samples was 2 µg/ml in the PA antigen test and 3.5 µg/ml in the hTSH test. Strips were washed over 2-3 minutes by adding drops on the wash buffer pad attached to the low portion of the Fusion 5 membrane and developed by adding 2 drops of substrate.

Results:

The test for detecting anthrax PA antigen required 5 minutes time. Concentrations as low as 2 ng/ml were detected. The hTSH test required 8 minutes time. Concentrations of antigen as low as 45 pg/ml (0.21 U/ml) were detected. The sensitivity in this range is sufficient to analyze the hTSH concentration in human blood to diagnose hypothyroidism, normal state or hyperthyroidism.

Example 16

Rapid Test for Detection of Antibodies to the T24 Cysticercosis Antigen on a Glass Fiber Membrane and Comparison with a Standard ELISA Test 1.2 µm CML particles conjugated with BSA-polyacrylic acid-DMPA/PEG-Biotin were applied at 2 µl/cm to make a test line on a Fusion 5 membrane. An internal control line was prepared using similar particles containing PQ and PEG without biotin mixed with particles containing anti-HRP IgG as described in Example 14. Strips were prepared as described in Example 14

For capture of antibodies specific to anti-T24 antigen in a test line, antigen-specific antibodies were sandwiched between StrAv and HRP conjugates and then captured through binding of StrAv to biotin in the test line. Recombinant T24 antigen from cysticerci of pork worm *T. solium* (92 aa, MW 10,013) was conjugated with StrAv and HRP at equimolar ratio using maleimide sulfhydryl conjugation chemistry (this approach is described in detail in U.S. Pat. Nos. 7,125,517 and 7,262,019). Two conjugates were used as a mixture containing 0.4 µg T24 antigen per ml of each conjugate, in diluents containing 10% calf sera in StabilZyme Select with 0.1% Tween-20 and 0.005% orange G dye. For testing, samples were diluted with sample diluents similar to conjugate diluents but containing 20% calf serum and 1×PBS. Equal volumes of diluted sample and a mixture of two antigen conjugates (StrAv and HRP) were combined and after a short (0.5-1 minute) incubation, 30 µl was applied on Fusion 5 strips. Strips were washed for 2-3 minutes by adding wash buffers with droppers, after which 2 drops of Substrate Solution were added on membranes not covered with clear film. The substrate reaction time was 5-6 minutes; however, for samples with high concentrations of the test analyte, the signal and internal positive controls became visible within 30 seconds after addition of the substrate.

ELISA versions of the test for detection of anti-T24 antibodies was run on plates coated with biotin-PEG-BSA. Diluted samples (50 µl) were added into wells and 50 µl conjugate mixture at 0.2 µg/ml of T24 antigen was added. Plates were incubated at shaking for 30 minutes, washed, and highly sensitive TMB substrate was added. The reaction time with substrate was 4 minutes with shaking. The reaction was stopped with 100 µl universal stop solution and read at 450 nm. Samples in both tests were panels of human sera containing samples from people afflicted with neurocysticercosis, non-*T. solium helminthic* infection, and normal human sera.

Results:

A comparison of the detection limits at testing of a cysticercosis positive serum pool in the rapid lateral flow test and ELISA described above show that the rapid lateral flow test can produce positive signals at dilutions of positive sera up to 40,960 times, whereas in the ELISA test, positive signal (OD~0.1) is produced at dilutions of up to 10,240 (FIG. 3). Comparison of the rapid test and ELISA testing a panel of positive sera, cross-reactive samples and normal sera (total 80 samples) demonstrates that all positive samples in the ELISA test, which included some very low positive samples with absorbance close to the cutoff value of the test (<0.2), are positive in the rapid test. All ELISA-negative samples are also negative in the rapid test.

Example 17

Rapid Lateral Flow Test for Lyme Disease with C6 and C10 Peptides on Glass Fiber Membranes The rapid lateral flow/dip-strip test for detection of antibodies against two diagnostic peptides of Lyme disease, C6 peptide (26 amino acids) and C10 peptide (10 amino acids), was created using particle- and soluble polymer-conjugated hydrogen donors and peptide conjugates. All peptide conjugates were prepared using peptides with N-terminal cysteine. The C6 peptide was coupled to maleimide-activated 0.78 µm amine particles, prepared by reaction with GMBS in 50 mM phosphate buffer, pH 7.6 containing 1 mM EDTA. Activated particles were washed with phosphate buffer, pH 6.5, containing 1 mM EDTA and reacted with Cys-C6 peptide at concentration 0.5 mg/ml. C10 peptide were covalently immobilized on 0.8 µm carboxylate particles loaded with BSA as described in Example 2. Sulfhydryl-reactive BSA particles with maleimide groups were obtained through modification of amino groups of BSA with GMBS in 50 mM phosphate buffer, pH 7.6, containing 1 mM EDTA. Maleimide-activated particles were purified by two centrifugations in 50 mM phosphate buffer, pH 6.5 with 1 mM EDTA and reacted with Cys-C10 peptide at a concentration of 0.2 mg/ml and particle in particle suspension at 2% solid.

Particles with immobilized C6 and C10 peptides were washed several times and finally resuspended in StabilGuard Choice with 0.05% PolyFox NP154. Both peptides were conjugated to maleimide-activated BSA and maleimide-activated StrAv. Ratios of peptides to protein were as follows: C6:BSA-4:1; C6:StrAv-2:1; C10:BSA-4:1; C10:StrAv-4:1.

Mixtures of particles for making test lines were prepared by mixing peptide-loaded particles and 0.8 μm DMPA or NED particles synthesized by loading carboxylate particles with BSA, polymaleic anhydride MW 5000 or polyacrylic acid MW 2000 and PEG as described in Example 2. The ratio of peptide particles to DMPA particles was 1:4. Particle suspension (2% solid) was stripped on Fusion 5 membrane at 1.5 μl/cm. Internal positive control line containing PQ as hydrogen donor and anti-HRP IgG was prepared as described in Example 2. Three lines were striped with 5 mm distance: internal positive control, C6 test containing DMPA particles and C10 test containing NED particles.

C6 peptide was conjugated to HRP using GMBS-activated enzyme at a ratio of peptide:HRP of ~1.5:1. C10 peptide was conjugated with HRP through BSA spacer using maleimide/sufhydril chemistry, comprising C10-BSA-HRP at ratio 4:1:3 as in U.S. Pat. No. 7,125,517. Peptide-HRP conjugates were used as solution with peptide concentration of 0.1 μg/ml, separately or mixed together, using conjugate diluents described in previous examples. For testing, 30 μl samples were mixed with 30 μl peptide-HRP conjugate, and 30 μl of the mixture was immediately transferred onto strips. Testing protocol was similar to that described in Example 16.1.

The ELISA test for detection of antibodies against C6 and C10 peptides was based on capture of antibody complexes with two peptide conjugates, peptide-StrAv and peptide-HRP, on plates coated with biotin-PEG-BSA as in U.S. Pat. No. 7,125,517 and Example 16. Three types of samples were used: a) affinity-purified anti-C6 IgG and anti-C10 IgM obtained from human sera containing high titer of anti-peptide antibodies; b) a panel of human sera with Lyme disease; and c) normal blood donors. Affinity-purified antibodies were spiked into normal human sera or into sample diluents containing 20% calf sera as described above.

Results:

Lateral flow/dip-strip test for detection of anti-C6 anti-C10 antibodies on strips of Fusion 5 membrane provides strong signal for highly positive samples within 2 minutes after adding the sample-conjugate mixture on Fusion 5 strips. The color development time for low positive samples is within 6 minutes. Samples containing anti-C6, anti-C10 or their mixture induce color formation only in corresponding specific capture zones, i.e. in the presence of anti-C6 antibodies, only C6 test line with violet color is visible (besides red internal positive control line). Likewise, in the presence of anti-C10 IgM, only blue C10 test line is visible, and both lines are visible when a mixture of C6 and C10 antibodies is present in the sample. The test is fairly resistance to false positive signals, so the negative result stays negative for up to 20 minutes after the substrate has been added onto the strips. Rapid test in this assay format can detect anti-C6 and anti-C10 antibodies in samples at concentration as low as 0.062 μg/ml. A corresponding ELISA test utilizing similar detection principles (capture antibodies as complex with two antigen conjugates) has a slightly lower sensitivity, with detection limit around 0.125 μg/ml. Testing of a Lyme patient panel with a known ELISA data, demonstrated that all ELISA-positive samples including very low positive with absorbance between 0.24 and 0.12 (ELISA cut-off), provided a positive signal in a rapid test. No false positive signals were detected in testing normal human sera. Samples containing antibodies against both peptides produce two easily discriminated colors in the test lines and internal positive control line. There is a good correlation between OD values in the ELISA test and the intensity of band staining in the rapid test.

Example 18

Rapid Lyme Peptide Lateral Flow/Dip-Strip Test on Fast Flow Nitrocellulose Membrane Both C6 and C10 peptides were conjugated to maleimide-activated BSA and maleimide-activated StrAv. The ratio of peptide: protein was as follows: C6:BSA-4:1, C6:StrAv-2:1, C10:BSA-4:1, and C10:StrAv-4:1. Soluble polymer-hydrogen donor conjugate mixtures were striped on 25 mm supported UniSart CN95 membrane (Sartorius) at 0.5 μl/cm. The internal positive control line was a mixture of PQ conjugate (BSA-PEG-polymaleic acid) and anti-HRP IgG at concentrations of 1 mg/ml and 0.25 mg/ml, respectively. The distance between lines was 5 mm.

The C6 test line contained mixtures in a PBS-EDTA buffer of BSA-PEG-polyacrylic acid-DMPA-PEG-biotin and C6-BSA at 2:1 ratio, with the BSA concentration in conjugates being 0.25 mg/ml and 0.75 mg/ml, respectively. The C10 test line mixture was made from the same type of hydrogen donor conjugate containing NED and BSA-C10 conjugate, 4:1.

Nitrocellulose membranes were laminated onto a 90 mm adhesive backing card, Fusion 5 membrane 25 mm was laminated as a wick contacting a wash buffer pad in an assembled cassette, and 25 mm cellulosic membrane was attached to the nitrocellulose membrane as an adsorbent pad. 5 mm strips were inserted into the bottom part of three holes of the plastic cassette for the lateral flow tests. Porous polyethylene (Porex 4785; 12-14 mm) was placed on one end of the Fusion 5 membrane as a wash buffer application pad and 4×24 mm cellulosic adsorbent type 901 (Pall) was placed on the distal end to provide additional capacity for wash buffer.

For sample testing, 15 μl of sample was mixed with 15 μl peptide-HRP conjugate containing Orange G dye and 12.5 μl was transferred to the nitrocellulose portion of the strip just before the C10 test line. Ten drops of wash buffer were added onto the wash buffer pad through the window. After complete clearance of Orange G dye from the nitrocellulose membrane (~2.5-3 minutes), one drop (25 μl) of substrate was added directly on to the test lines.

Results:

The positive control line and strong and medium positive samples produced colored lines in seconds after contact with substrate. The rapid test utilizing lateral flow principles with an HRP label and new substrate system applied on a fast nitrocellulose membrane demonstrated positive results in a short time, (close to 3 minutes). Low positive samples required up to 5 minutes for color development. Blank samples (sample diluents only) and negative samples did not produce false-positive staining at least during additional 5 minutes after test completion. Test lines were sharp and bright for high positive results. All lines in the multicolor picture had easily discriminated colors. Sharpness of lines in a test on nitrocellulose membranes prepared by passive adsorption of water-soluble reagents is better than in a test on glass fiber membranes containing particle-based reagents. The sensitivity of the new rapid Lyme test on fast nitrocellulose membrane exceeded the sensitivity of the ELISA test of the same format, utilizing peptide conjugates by several-fold.

Example 19

Rapid Lateral Flow Lyme Peptide Test on Porous Polyethylene Strips Comparison with TMB Substrate 0.8 μm particles with immobilized hydrogen donors and their mixtures with other particles containing BSA-C6 peptide were applied by pipette on 12×50 mm strips of Porex 4897 porous polyethylene matrix. Particles for internal positive control, 1.2 μm were covalently immobilized with anti HRP polyclonal antibodies. Mixtures contained particles with immobilized hydrogen donors 1.5% solid and 0.5% solid particles with C6-BSA or anti HRP antibodies. In StabilGuard Choice with 0.1% PolyFox NP-154 in PBS-EDTA and 4% sucrose. Dispensing volume was 2.0 μl/cm. Similar strips were prepared by spotting only C6-BSA particles and control anti-HRP particles 1% solid for use with the TMB substrate system. Strips were laminated onto backing cards with an adhesive and dried at 45° C. for 15 minutes in a food dehydrator. Thick adsorbent material was attached to strips from the positive control spot end. For testing, sera samples were mixed with 2 volumes of C6-HRP conjugate, 5 μg/ml in conjugate diluents containing 10% calf sera, PBS, 0.2% triton X-100 and Orange G as a tracking dye and after a short incubation (20-30 seconds) 100 μl applied onto strips below the test spots. Strips were washed during 2-3 minutes by adding wash buffer on the end of the strips below the sample application zone until all the tracking dye was adsorbed. Strips with hydrogen donor particles were developed by adding 4 drops of MBTH/sodium perborate substrate (Example 7.1) and strips without hydrogen donors were developed by adding TMB substrate (Moss, Inc.). Pictures were taken after 4-5 minutes.

Results:

Small sera panels containing two low positive, one medium and two strong positive tests with the new substrate system easily detected all samples as positive, whereas the TMB test demonstrated a false negative result for one low positive sample and a very weak signal for another low positive sample. Spots developed with TMB substrate were not as sharp nor easy to read as spots produced on strips with the new substrate system. (See FIG. 6).

Example 20

Flow-Through Test for Detection of Antibodies Against C6 and C10 Peptides

Soluble reagents for detection of anti-Lyme peptide antibodies (See Example 17) were applied for the development of a flow-through test. In one experiment, 0.6 μl of mixtures for positive control, C6 and C10 test were applied on squares of nitrocellulose membrane 22×22 mm with paper backing (Whatman CF 060, 0.6 μm pore size). In a second experiment, reagents were applied in diagnostic membranes as lines with a short dotted middle line for positive control and two longer solid lines at a distance of 4 mm from the central positive control line, containing C6-BSA and BSA-hydrogen donor conjugates. After drying, membranes were inserted into flow-through barrel type cassettes with a round 15 mm window on the top part. As an adsorbent, thick polyether material was placed below the nitrocellulose membrane.

Samples were prepared by dilution (1:200) in sample diluents containing 20% calf sera in StabilZyme Select. For preparation of positive human sample with serial dilutions, the first dilution was made with a sample diluent containing 20% calf sera and subsequent dilutions with diluents containing 20% calf sera and 1:200 normal human sera. As a detector conjugate, a F(ab')2 fragment of goat IgG against human IgG-HRP (Jackson Immunoresearch) at a concentration of 6 μg/ml in conjugate diluents (Example 17) was used.

A 50 μl sample was mixed with 50 μl HRP conjugate and after 30 seconds, incubation transferred into cassette pre-washed with 3 drops of wash buffer. After complete adsorption of the sample/conjugate through test membranes, cassettes were incubated for about 1 minute and 4 drops of wash buffer were added. After complete adsorption, washing was repeated three more times by adding 5-6 drops of wash buffer. Finally, three drops of substrate were added.

Figure 7:
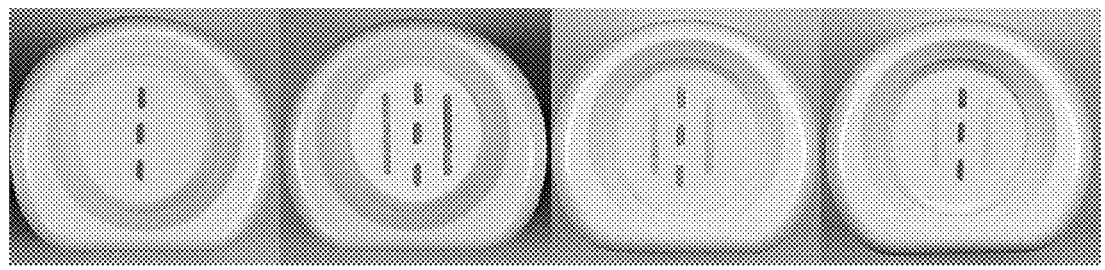
FIG. 7 is a photograph showing the results of flow through tests for the detection of antibodies against the Lyme peptides C6 and C10. Test and positive control lines were prepared with soluble hydrogen donor conjugates striped on a paper backed nitrocellulose diagnostic membrane. Test lines contained DMPA (C6 test) and NED (C10 tests) hydrogen donor conjugates mixed with C6-BSA and C10-BSA correspondingly. The positive control zone was a mixture of a PQ-BSA-polymer conjugate with anti-HRP antibodies. Positive Lyme sera contained antibodies against both C6 and C10 peptides.
Figure 4:
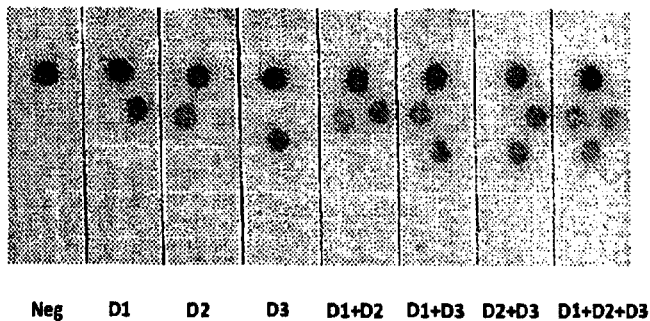
Figure 6:
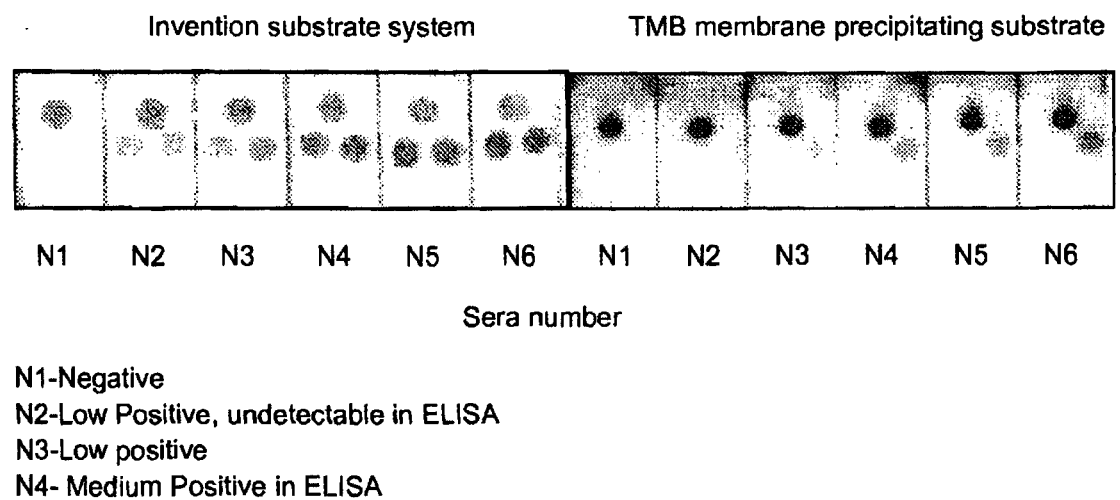
Figure 7:
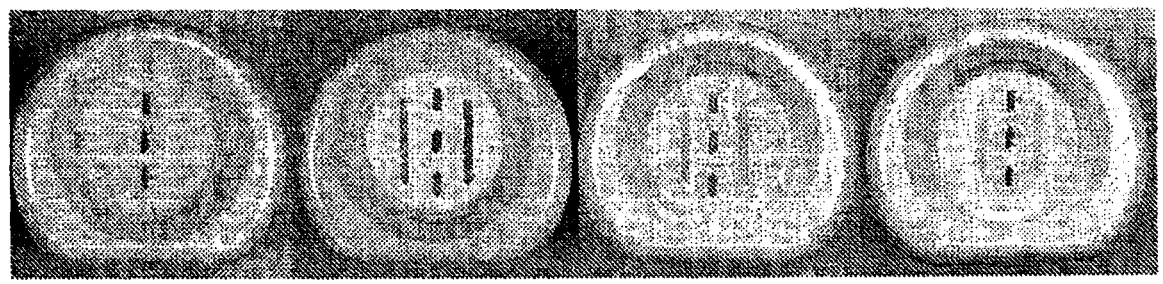

Results:

A flow-through test in this configuration required approximately 4 minutes time to complete and produced sharp, free from background staining with multicolor pictures for positive samples (FIG. 7). In testing high positive Lyme patient samples, positive signals can be detected at dilutions of up to 100,000 times, which is comparable to the sensitivity of the ELISA test which uses a similar antibody detection format but requires 1.5 hours to assay.

Example 21

Lateral Flow/Dip-Strip Test for Detection of Antibodies Against HIV Peptide

A rapid test for detecting anti-HIV-1 peptide IgG antibodies was prepared using soluble reagents applied on the fast nitrocellulose membrane CN95. HIV 1 immunodominant peptide antigen from the gp 41 protein was synthesized in monobiotinylated form through modification with Biotin-PEG-SVA MW5K. The biotinylated PEG-peptide was mixed with SAtrAv at molar ratio 3:1 The test line on NC95 was prepared using a soluble hydrogen donor conjugate BSA-PEG-polyacrylic acid-NED-PEG. A mixture StrAv-Biotin-PEG-peptide and BSA-donor conjugates at concentrations of 0.5 mg/ml and 1 mg/ml, respectively, was striped on membranes at 1.0 μl/cm. Wash buffer and adsorbent pads were prepared as described above. For testing, HIV positive samples were diluted with sample diluent containing 20% calf sera in StabilZyme Select with PBS, 1 mM ETDA, 0.2% Triton X-100 and 0.1% Tween-20. Diluted samples were mixed with equal volumes of goat anti-human IgG-Fc-HRP conjugate at a concentration of 4 μg/ml and after short incubation (10-15 seconds) 12.5 μl was transferred onto the strip. Washing and substrate reactions were done as described above.

An ELISA test with a similar antibody detection format was run on plates coated with BSA-G1 peptides at 4 μg/ml. Samples were diluted with sample diluents and incubated while shaking for 30 minutes. After washing, goat anti-human IgG-Fc-HRP conjugate was added and plates were incubated for 25 minutes while shaking Washed wells were developed with the ultrasensitive TMB substrate (4 min with shaking) and stopped with the Universal stop solution.

Results:

This ELISA could detect anti-gp41 peptide antibodies in one arbitrarily selected high positive serum sample at dilutions up to 400,000 times (FIG. 8B). Lateral flow test with assay time of 8 minutes produce highly visible signals on strips at dilutions at least 6 million (FIG. 8 A) The test could easily detect antibody in all samples of HIV-positive panels, including very low positives at ELISA testing. Testing of normal blood donors demonstrated no false positive signals, as well as a high resistance to the appearance of false positive results upon extension of read time for several minutes. These data confirmed the high specificity of this test, Example 22

Rapid Test for Detection of Pseudoperoxidase Activity of Human Hemoglobin

Rabbit anti-human hemoglobin antibodies (Medix Biochemica, Finland) were immobilized on 0.8 μm CML particles activated with EDAC/NHS. For making test lines containing immobilized hydrogen donor and anti-hemoglobin antibodies, particles were mixed in equal amounts with 1.5 µm CML particles loaded with DMPA/PEG. Mixtures (2% solid) were striped on Fusion 5 membranes at 1.5 µl/cm.

Standard solutions of human hemoglobin (from Sigma) were prepared in PBS with 5 mg/ml BSA. For testing, 50 µA of hemoglobin solution in PBS-BSA was added onto strips. Strips with attached adsorbent pad were washed by adding 6-8 drops of wash buffer during 2 minutes and 3 drops of substrate were added close to the capture line. Result were read after 5 minutes Results:

Strips of fast glass fiber membrane with particles containing hydrogen donors and particles binding human hemoglobin produced visible color at concentrations of hemoglobin in the sample as low as 6.25 µg/ml.

Example 23

Test Utilizing Hydrogen Peroxide Generated from Glucose Oxidase Co-Immobilized with Hydrogen Donors on Membranes or Captured Together with Horseradish Peroxidase (HRP) Conjugates Two types of reagents containing glucose oxidase were prepared: a) glucose oxidase (Sigma) covalently immobilized on 1.6 µm carboxyl polystyrene latex (CM) particles, and b) glucose oxidase-HRP-T24 chimeric conjugates at ratios of 1:1:1 using maleimide/sulfhydryl cross-linking reagents. Two types of test lines were made on Fusion 5 membranes. One contained a mixture of 1.6 µm particles with immobilized glucose oxidase and 1.2 µm carboxylate-modified polystyrene latex (CML) particles with PQ/PEG-biotin at ratio 1:1. The second contained only CML particles with PQ/PEG-biotin. Mixtures were striped on membrane at 2 µl/cm. Strips were prepared as described above.

Two substrates were used: one as described above, containing 1 mM MBTH and 4 mM sodium perborate, and the second which had 50 mM glucose instead of sodium perborate. Lateral flow/dip-strip tests for detection of antibodies against cysticercosis antigen T24 were conducted in an antibody capture format utilizing two antigen conjugates as described above. Three versions of the rapid T24 antibody test were run in parallel. The first was identical to test above, which used strips with particles containing PQ/biotin and a mixture of T24-StrAv and T24-HRP conjugates for antibody capture and standard MBTH/sodium perborate substrate. The second test used strips with a mixture of PQ/biotin particles and glucose oxidase particles, the same antigen conjugate mixture, and MBTH/sucrose substrate. The third test was identical to the first, but with a mixture of T24-StrAv/T24-glucose oxidase-HRP and MBTH/sucrose substrate. Human sera containing antibodies against T24 antigen were used for comparing the sensitivity of these tests Results:

All versions of the test had similar detection limits of serially diluted positive sera samples. The amount of hydrogen peroxide generated by glucose oxidase/sucrose on membrane in close proximity to hydrogen donors and captured HRP was enough for efficient oxidation of the MBTH coupler and its coupling with immobilized hydrogen donors. However, the kinetics of dye formation in the test with the glucose oxidase/sucrose pair as a source of peroxide was slightly slower. While the test with MBTH/perborate took 3 minutes to attain a good signal intensity, the test with glucose oxidase required about 6 minutes for color development of the same intensity.

Example 24

Tests with Oxidizable Coupling Reagent and the Peroxide Substrate Dried on a Porous Material Several methods for preparing dry forms of MBTH/sodium perborate substrate were found. As an example, substrate prepared in a MES-borate-EDTA drying buffer described above was applied on squares of porous materials such as porous polyethylene (Porex X-4897), glass fiber membranes, Fusion 5 and GF/DNA (Whatman) and dried in a freeze-dryer overnight. Alternatively, porous materials saturated with liquid substrate were kept for 15 minutes at 45° C. and then in a vacuum oven at room temperature overnight in the presence of desiccant.

Pieces of materials with dry substrates were placed on strips after completion of washing and substrates were eluted by adding wash buffer in a volume corresponding to a liquid-absorbing capacity of material with dry substrate.

Results:

Substrate dried on porous materials such as porous polyethylene and glass fiber membrane preserved activity and could be quickly eluted using wash buffer with low buffering capacity and delivered into diagnostic zones for chromogenic reaction with immobilized hydrogen donors. The activity of substrates dried on some porous materials was comparable to the activity of the original liquid form. Substrate dried on porous materials is suitable for long storage if packed in the presence of desiccant and protected from light.

INCORPORATION BY REFERENCE

The contents of all cited references including literature references, issued patents, published or non published patent applications as cited throughout this application are hereby expressly incorporated by reference. Additionally, the following references are expressly incorporated herein by reference: U.S. Pat. No. 5,556,743 Gibboni et al.; U.S. Pat. No. 4,999,287 Allen et al.; U.S. Pat. No. 5,155,025 Allen et al.; U.S. Pat. No. 5,409,780 Schrier et al.; EP Patent No. 0345460 Abbott Laboratories; U.S. Pat. No. 5,432,285 Spyros Theodoropulos; T. T Ngo and H. M. Lenhoff (Anal Biochem, 1980, 105, 389-370); U.S. Pat. No. 5,726,010 IDEXX; U.S. Pat. No. 6,436,722 IDEXX; U.S. Pat. No. 7,442,557 IDEXX; Polyethyleneglycol chemistry, Biotechnical and biomedical applications, Ed by J. Milton Harris, Plenum Press, 1992; Conyers, S M, Kidwell D A. *Anal Biochem,* 1991, 192: 207-211; U.S. Pat. No. 6,960,323 Guo S. X. et al.; Georghegan et al, *J Immunol Methods,* 1983, 60, 61-68; U.S. Pat. No. 6,635, 439 Morrison et al.; U.S. Pat. No. 5,824,491 Priest et al.; U.S. Pat. No. 5,972,294 Smith et al.; U.S. Pat. No. 5,922,530 Yu Yeung; U.S. Pat. No. 6,218,571 Xiaoling Zheng at al.; U.S. Pat. No. 6,858,401 Phillips at al.; U.S. Pat. No. 6,531,322 Jurik at al.; U.S. Pat. No. 5,532,138 Singh S. at al.; U.S. Pat. No. 5,024,935 McClune et al.; U.S. Pat. No. 5,457,200 Zimmermann at al.; U.S. Pat. No. 5,910,423 Yamazaki et al.; U.S. Pat. No. 5,710,012; U.S. Pat. No. 6,242,207; U.S. Pat. No. 5,992,530; U.S. Pat. No. 4,962,040; U.S. Pat. No. 5,532,138; U.S. Pat. No. 5,563,031; U.S. Pat. No. 6,379,915; U.S. Pat. No. 5,710,012; Li et al. Analyt Biochem, 1987, 166, 276-83; Zuk et al. Clin Chem, 1985, 7, 1144-50; and U.S. Pat. No. 6,706,539.

EQUIVALENTS

Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed.

The invention claimed is:

1. A composition of water soluble hydrogen donor polymer conjugates, said composition being capable of reacting with an electron acceptor/coupler, a peroxide, and a compound having peroxidative activity, wherein upon reaction said composition produces a colored reaction product, the composition comprising hydrogen donors covalently linked to copolymers of water soluble polycarboxylic polymers, uncharged hydrophilic polymers, and hydrophilized protein carrier.

2. The composition of claim 1, wherein the hydrogen donors are selected from the group consisting of amine-containing compounds comprising substituted anilines, quinolines, naphthols, and phenols, which hydrogen donors produce dyes of different colors with absorbance maxima in a range of 380-650 nm in a reaction with oxidized coupler.

3. The composition of claim 1, wherein the hydrogen donors are 8-[4-amino-1-methylbutyl]-6-methoxy quinoline, N,N-Dimethyl-1,3-phenylenediamine, N-Phenylethylenediamine, or N-(1-Naphthyl)ethylenediamine.

4. The composition of claim 1, wherein the polycarboxylic polymers are branched pendant carboxylic polymers or linear polymers.

5. The composition of claim 4, wherein the linear polymer is selected from polyglutamic acid, polyaspartic acid, polyacrylic acid, polymaleic acid, polymethacrylic acid, polyacrylamide/polyacrylic acid copolymer, polyvinyl-maleic acid copolymer, polyethylene maleic acid copolymer, and polyacrylic-polymaleic acid copolymer.

6. The composition of claim 1, wherein the uncharged hydrophilic polymers are polyethylene glycols of various molecular weights in the range of 1-20 kDa.

7. The composition of claim 1, wherein the protein carrier is bovine serum albumin additionally hydrophilized by attachment of polyethylene glycols through amino or carboxyl groups of the protein.

8. The composition of claim 1, wherein the water soluble hydrogen donor conjugates are immobilized on particles through non-covalent passive adsorption.

9. The composition of claim 1, wherein the uncharged hydrophilic polymer or hydrophilized protein carrier further contains a member of a binding pair.

10. The composition of claim 9, wherein the member of the binding pair is biotin.

11. A method for detecting a compound having peroxidative activity comprising:

(a) providing:
(i) the composition of hydrogen donor polymer conjugates of claim 1,
(ii) an electron acceptor/coupler,
(iii) a peroxide, and
(iv) a reagent comprising a compound having peroxidative activity;
(b) reacting the components of (i), (ii), (iii), and (iv), wherein in the presence of a compound having a peroxidative activity, a colored reaction product is produced.

12. The method of claim 11, wherein the hydrogen donor polymer conjugates are incorporated into zones of a diagnostic membrane.

13. The method of claim 12, wherein a plurality of different hydrogen donor conjugates incorporated into different zones of the membrane allows for the detection of a plurality of analytes producing a specific color for each analyte.

14. The method of claim 12 or 13, wherein the hydrogen donor polymer conjugates are applied to the membrane by passive adsorption.

15. The method of claim 14, wherein the method further comprises using the membrane as a medium in lateral flow chromatographic separation, vertical filtration, passive diffusion, bead filtration, a dip-stick or a slide microarray assay.

16. The method of claim 14, wherein the hydrogen donor polymer conjugates are mixed with soluble analyte capture reagents and applied to the membrane.

17. The method of claim 12 or 13, wherein the hydrogen donor polymer conjugates are immobilized on particles and the particles are applied to the membrane by trapping the particles in pores.

18. The method of claim 17, wherein the method further comprises using the membrane as a medium in lateral flow chromatographic separation, vertical filtration, passive diffusion, bead filtration, a dip-stick or a slide microarray assay.

19. The method of claim 17, wherein the particle-bound hydrogen donor polymer conjugates are mixed with particle-bound analyte capture reagents and applied to the membrane.

20. The method of claim 11, wherein the electron acceptor/coupler is 3-Methyl-2-benzothiazolinone hydrazine or a derivative thereof.

21. The method of claim 11, wherein the peroxide is selected from sodium perborate, hydrogen peroxide and urea hydrogen peroxide.

22. The method of claim 21, wherein the peroxide is provided by the conversion of a substrate of an oxidative enzyme.

23. The method of claim 11, wherein the peroxidase is a reagent serving as a detector label for detecting and/or quantifying an analyte.

24. The method of claim 23, wherein the peroxidase is selected from a horseradish peroxidase, another plant peroxidase, or a microperoxidase.

25. A method of making a reagent comprising coupling the water soluble hydrogen donor polymer conjugates of claim 1 to particles through non-covalent passive adsorption or covalent linking with carboxylate or aminated particles.

* * * * *

UNITED STATES PATENT AND TRADEMARK OFFICE
CERTIFICATE OF CORRECTION

| | | |
|---|---|---|
| PATENT NO. | : 8,815,532 B2 | Page 1 of 6 |
| APPLICATION NO. | : 13/478820 | |
| DATED | : August 26, 2014 | |
| INVENTOR(S) | : Victor Kovalenko | |

It is certified that error appears in the above-identified patent and that said Letters Patent is hereby corrected as shown below:

In the Drawings

Replace Figures. Figures 3A, 3B, 4, 5A, 6, and 7 on Drawing Sheets 3-7 with the enclosed corrected Figures 3A, 3B, 4, 5A, 6, and 7 on the attached sheets.

Signed and Sealed this
Twenty-fourth Day of March, 2015

Michelle K. Lee
*Director of the United States Patent and Trademark Office*

FIGURE 3
A. Fusion 5 glass fiber membrane (Assay time 2 min)
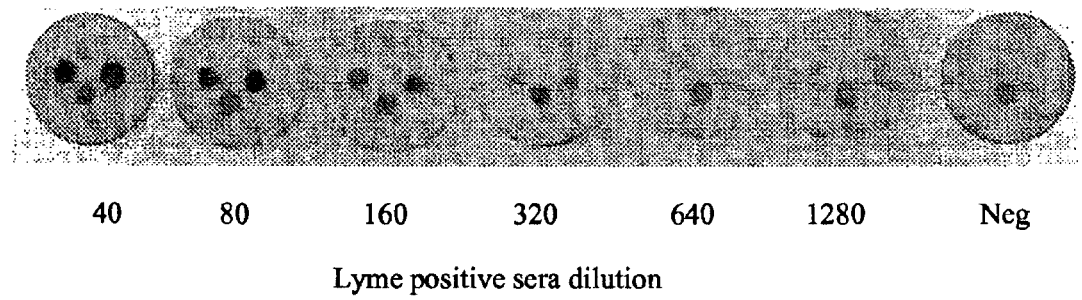
40　　80　　160　　320　　640　　1280　　Neg
Lyme positive sera dilution
B. Porous polyethylene matrix (Assay time 4-5 min)
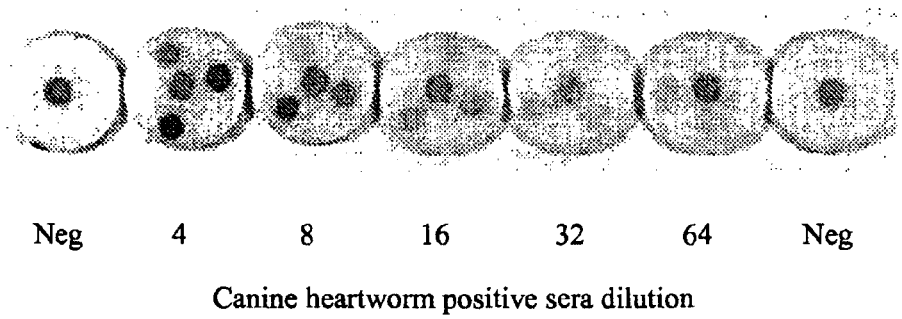
Neg　　4　　8　　16　　32　　64　　Neg
Canine heartworm positive sera dilution Neg- Negative sample, internal control spot-Violet
D1 positive test spot-Blue
D2 positive test spot-Red
D3 positive test spot-Rose
D1+D2 positive test spots-Red and Blue
D1+D3 positive test spots-Red and Rose
D2+D3 positive test spots-Blue and Rose
D1+D2+D3 positive test spots-Red, Blue and Rose

FIGURE 5
A.
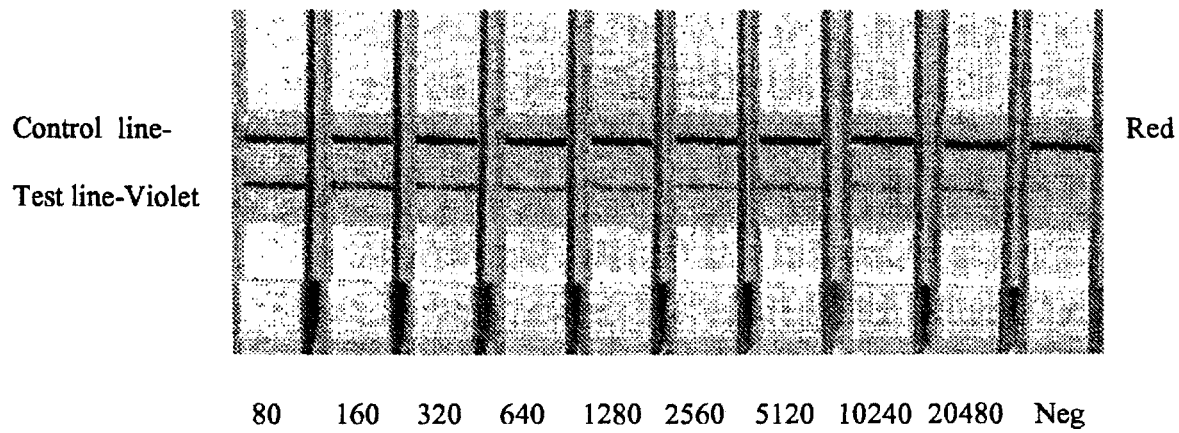
B.
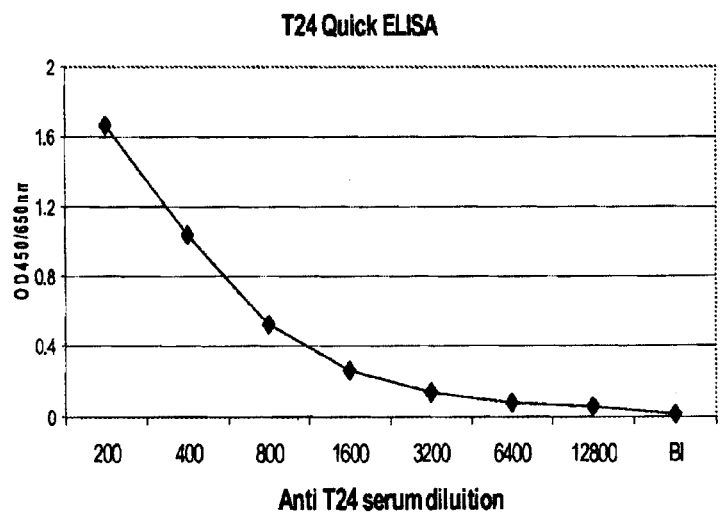

Figure 6:
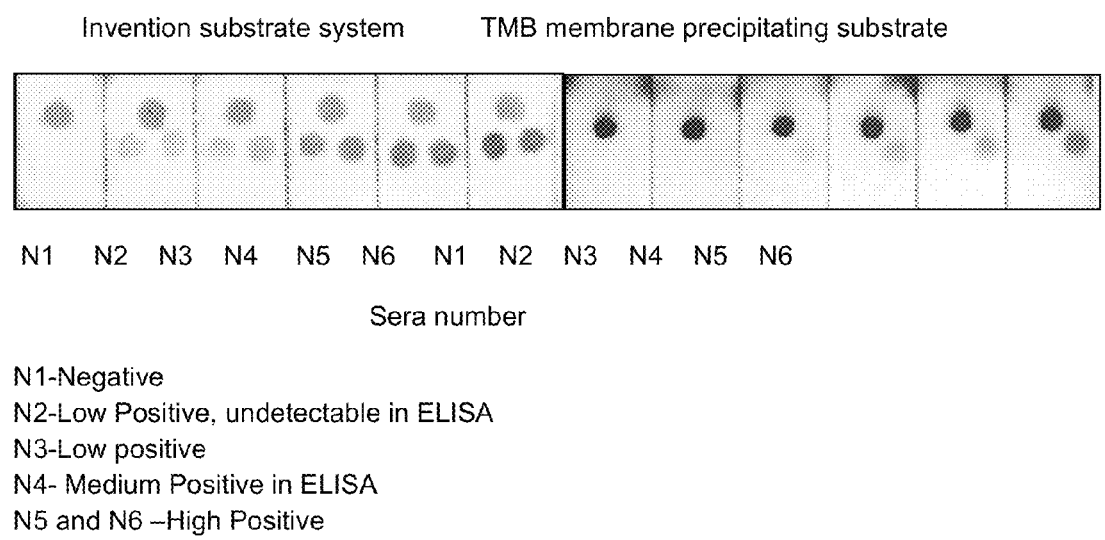
FIG. 6 is a photograph showing the results of lateral flow tests for the detection of antibodies against Lyme C6 peptide antigen in serial dilutions of one positive sample. Porous polyethylene (Porex 4897) strips were spotted with particle-bound reagents. Two test spots contain particle bound DMPA and NED hydrogen donors applied together with particles containing antigen, C6-BSA. The positive control spot contained PQ particles and particle-bound anti-HRP antibodies. For testing with TMB, substrate strips were spotted with particles containing only C6-BSA (Test spot) or anti HRP antibodies (Positive control spot). Samples were mixed with C6-HRP and applied on strips. After washing by lateral flow mechanism, aliquots of substrates were added onto the strips. Upon addition of substrate containing MBTH and sodium perborate, the two test spots produced violet (DMPA) or blue (NED) spots and red for positive control. Strips developed with TMB substrate produced a greenish color.

FIGURE 6 Lateral Flow test for detection of antibodies against Lyme C6 peptide on Porex porous polyethylene strips N1-Negative
N2-Low Positive, undetectable in ELISA
N3-Low positive
N4- Medium Positive in ELISA
N5 and N6 –High Positive Flow-through test on nitrocellulose membrane (Assay time 5-8 min)

Neg      1:80      1:5,120      1:81,920

Lyme positive sera dilution

Middle dashed line-internal positive control (Red)
Left solid line- C6 Test (Violet)
Right solid line – C10 test (Blue)